(12) United States Patent
Kimoto

(10) Patent No.: US 8,417,105 B2
(45) Date of Patent: Apr. 9, 2013

(54) IN-VIVO INFORMATION DISPLAY DEVICE, IN-VIVO INFORMATION DISPLAY SYSTEM, AND IN-VIVO INFORMATION DISPLAY METHOD

(75) Inventor: Seiichiro Kimoto, Akiruno (JP)

(73) Assignee: Olympus Medical Systems Corp., Tokyo (JP)

( * ) Notice: Subject to any disclaimer, the term of this patent is extended or adjusted under 35 U.S.C. 154(b) by 636 days.

(21) Appl. No.: 12/580,611

(22) Filed: Oct. 16, 2009

(65) Prior Publication Data

US 2010/0099948 A1    Apr. 22, 2010

(30) Foreign Application Priority Data

Oct. 17, 2008    (JP) .................... 2008-268897

(51) Int. Cl.
*A61B 1/04*    (2006.01)
(52) U.S. Cl. .......... 396/109; 600/117; 600/118
(58) Field of Classification Search .......... 600/101, 600/117, 118, 109
See application file for complete search history.

(56) References Cited

U.S. PATENT DOCUMENTS

| | | |
|---|---|---|
| 6,416,471 B1 | 7/2002 | Kumar et al. |
| 2006/0001550 A1 | 1/2006 | Mann et al. |
| 2007/0002970 A1 | 1/2007 | Cornelius |
| 2007/0299301 A1 | 12/2007 | Uchiyama et al. |
| 2008/0242931 A1 | 10/2008 | Nishino |

FOREIGN PATENT DOCUMENTS

| | | |
|---|---|---|
| JP | 3-238542 A | 10/1991 |
| JP | 9-219715 A | 8/1997 |
| JP | 2006-180945 A | 7/2006 |
| JP | 2007-75164 | 3/2007 |
| JP | 2007-143648 A | 6/2007 |

OTHER PUBLICATIONS

Extended European Search Report dated Dec. 23, 2009.
Japanese Office Action dated Feb. 5, 2013 from corresponding Japanese Patent Application No. JP 2008-268897, together with an English language translation.

*Primary Examiner* — Rochelle-Ann J Blackman
(74) *Attorney, Agent, or Firm* — Scully, Scott, Murphy & Presser, P.C.

(57) ABSTRACT

An in-vivo information display device includes a communication unit that communicates with a receiving device that receives in-vivo information transmitted, at a predetermined time interval, from a body-insertable device that is introduced into a subject and acquires the in-vivo information regarding an inside of the subject; a transmission requesting unit that transmits a transmission request for the in-vivo information to the receiving device via the communication unit; and a display unit that displays the in-vivo information received via the communication unit from the receiving device in response to the transmission request. The transmission requesting unit transmits the transmission request to the receiving device at a first time interval smaller than the predetermined time interval, and the transmission requesting unit transmits the transmission request to the receiving device at a second time interval larger than the first time interval when one or more the in-vivo information is received.

20 Claims, 18 Drawing Sheets

IN-VIVO INFORMATION DISPLAY DEVICE, IN-VIVO INFORMATION DISPLAY SYSTEM, AND IN-VIVO INFORMATION DISPLAY METHOD

CROSS-REFERENCE TO RELATED APPLICATIONS

This application is based upon and claims the benefit of priority from Japanese Patent Application No. 2008-268897, filed Oct. 17, 2008, the entire contents of which are incorporated herein by reference.

BACKGROUND OF THE INVENTION

1. Field of the Invention

The present invention relates to an in-vivo information display device, an in-vivo information display system, and an in-vivo information display method. More particularly, the invention relates to an in-vivo information display device, an in-vivo information display system, and an in-vivo information display method, by which in-vivo information acquired by a body-insertable device introduced into a subject can be displayed to a user in substantially real time.

2. Description of the Related Art

A conventional system is well known in which a receiving device placed outside a subject such as a living body receives image data acquired by a body-insertable device introduced into the subject and a display device connected to the receiving device via a predetermined line displays the image data in real time. Such a system is known as disclosed in, for example, Japanese Patent Application Laid-open No. 2007-75164. In this conventional system, an image signal and a synchronizing signal are transmitted from the receiving device to the display device. The display device displays an intra-subject image acquired by a capsule-shaped body-insertable device to a user in substantially real time by displaying the received image signal in synchronization with the synchronizing signal.

In recent years, with the advance of information processing technology, it has been requested to display an image acquired by the body-insertable device by using an device, such as a personal computer, which has high general versatility and display function. It is normal to use an interface technology having high versatility such as a universal serial bus (USB) interface for the connection between an information processing device such as a personal computer and the receiving device.

When the information processing device is connected to the receiving device, the information processing device is the main device (master) and the receiving device is the sub device (slave) in terms of the connection relation between them. Therefore, when the information processing device acquires image data from the receiving device, it is required that the information processing device (master) requests the receiving device (slave) to transmit the image data and the receiving device transmits the image data to the information processing device in response to the request. This is referred to as a pull-type communication protocol.

SUMMARY OF THE INVENTION

An in-vivo information display device according to an aspect of the present invention includes a communication unit that communicates with a receiving device that receives in-vivo information transmitted, at a predetermined time interval, from a body-insertable device that is introduced into a subject and acquires the in-vivo information regarding an inside of the subject; a transmission requesting unit that transmits a transmission request for the in-vivo information to the receiving device via the communication unit; and a display unit that displays the in-vivo information received via the communication unit from the receiving device in response to the transmission request. The transmission requesting unit transmits the transmission request to the receiving device at a first time interval smaller than the predetermined time interval, and the transmission requesting unit transmits the transmission request to the receiving device at a second time interval larger than the first time interval when one or more the in-vivo information is received.

An in-vivo information display device according to another aspect of the present invention includes a communication unit that communicates with a receiving device that receives in-vivo information transmitted, at a predetermined time interval, from a body-insertable device that is introduced into a subject and acquires the in-vivo information regarding an inside of the subject; a transmission requesting unit that transmits a transmission request for the in-vivo information to the receiving device via the communication unit; and a display unit that displays the in-vivo information received via the communication unit from the receiving device in response to the transmission request. The transmission requesting unit transmits the transmission request to the receiving device; and the transmission requesting unit transmits, when the in-vivo information according to the transmission request is received, a next transmission request to the receiving device.

An in-vivo information display system according to still another aspect of the present invention includes a body-insertable device that is introduced into a subject and includes an in-vivo information acquiring unit that acquires information regarding an inside of the subject and a transmitting unit that transmits the in-vivo information as a radio signal at a predetermined time interval; a receiving device that is arranged outside the subject and includes a receiving unit that receives the in-vivo information transmitted from the transmitting unit and a first communication unit that communicates via a predetermined line; and an in-vivo information display device that includes a second communication unit that communicates with the first communication unit via the predetermined line and a display unit that displays the in-vivo information received via the second communication unit. The in-vivo information display device further includes a transmission requesting unit that transmits a transmission request for the in-vivo information to the receiving device via the second communication unit at a first time interval smaller than the predetermined time interval, and that transmits the transmission request to the receiving device via the second communication unit at a second time interval larger than the first time interval when one or more the in-vivo information is received. The receiving device transmits the in-vivo information received from the body-insertable device to the in-vivo information display device via the first communication unit in response to the transmission request.

An in-vivo information display system according to still another aspect of the present invention includes a body-insertable device that is introduced into a subject and includes an in-vivo information acquiring unit that acquires information regarding an inside of the subject and a transmitting unit that transmits the in-vivo information as a radio signal at a predetermined time interval; a receiving device that is arranged outside the subject and includes a receiving unit that receives the in-vivo information transmitted from the transmitting unit and a first communication unit that communicates via a predetermined line; and an in-vivo information display device that includes a second communication unit that communicates with the first communication unit via the predetermined line and a display unit that displays the in-vivo information received via the second communication unit. The in-vivo information display device further includes a transmission requesting unit that transmits a transmission request for the in-vivo information to the receiving device via the second communication unit, and that transmits, when the in-vivo information according to the transmission request is received, a next transmission request to the receiving device via the second communication unit. The receiving device transmits the in-vivo information received from the body-insertable device to the in-vivo information display device via the first communication unit in response to the transmission request.

An in-vivo information display method according to still another aspect of the present invention includes transmitting a transmission request for in-vivo information to a receiving device that receives the in-vivo information transmitted, at a predetermined time interval, from a body-insertable device that is introduced into an inside of a subject and acquires the in-vivo information regarding the inside of the subject; receiving the in-vivo information transmitted from the receiving device in response to the transmission request; and displaying the received in-vivo information. The transmitting a transmission request includes transmitting the transmission request to the receiving device at a first time interval smaller than the predetermined time interval; and transmitting the transmission request to the receiving device at a second time interval larger than the first time interval when one or more the in-vivo information is received.

An in-vivo information display method according to still another aspect of the present invention includes transmitting a transmission request for in-vivo information to a receiving device that receives the in-vivo information transmitted, at a predetermined time interval, from a body-insertable device that is introduced into an inside of a subject and acquires the in-vivo information regarding the inside of the subject; receiving the in-vivo information transmitted from the receiving device in response to the transmission request; and displaying the received in-vivo information. The transmitting a transmission request includes transmitting the transmission request to the receiving device; and transmitting, when the in-vivo information according to the transmission request is received, a next transmission request to the receiving device.

A computer program product according to still another aspect of the present invention has a computer readable medium including programmed instructions, wherein the instructions, when executed by a computer, cause the computer to perform the method according to the present invention.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of the present invention will be explained in detail below with reference to the accompanying drawings. However, the present invention is not limited to these embodiments. In the following descriptions, the shape, size, and positional relationship illustrated in each drawing are just schematic examples such that the contents of the present invention can be understood. Therefore, the present invention is not limited to the shape, the size, and the positional relationship illustrated in each drawing. For the clarity of the configuration, some of cross-sectional hatching in each drawing is omitted. Moreover, numeric values to be described below are only a preferable example of the present invention. Therefore, the present invention is not limited to these numeric values.

First Embodiment

Hereinafter, the configuration and operation of a medical system 1 according to the first embodiment of the present invention will be explained in detail with reference to the drawings. As a body-insertable device of the present embodiment, there is used a capsule medical device 10 that acquires information (in-vivo information) for the inside of a subject 100 on the way from the esophagus to the anus of the subject 100 after being introduced into the subject 100 via the oral route. However, the present invention is not limited to this. For example, various body-insertable devices can be used, such as a capsule medical device that acquires some kind of in-vivo information for the inside of the subject 100, in a state where the device is held in various types of organs such as a stomach or an intestine of the subject 100. Moreover, as in-vivo information acquired by the capsule medical device 10, there is used images (intra-subject images) captured by an imaging unit 15 to be described below. However, the present invention is not limited to this. Various information can be used, such as a temperature, a pressure, or a pH value for the inside of the subject.

Figure 1:
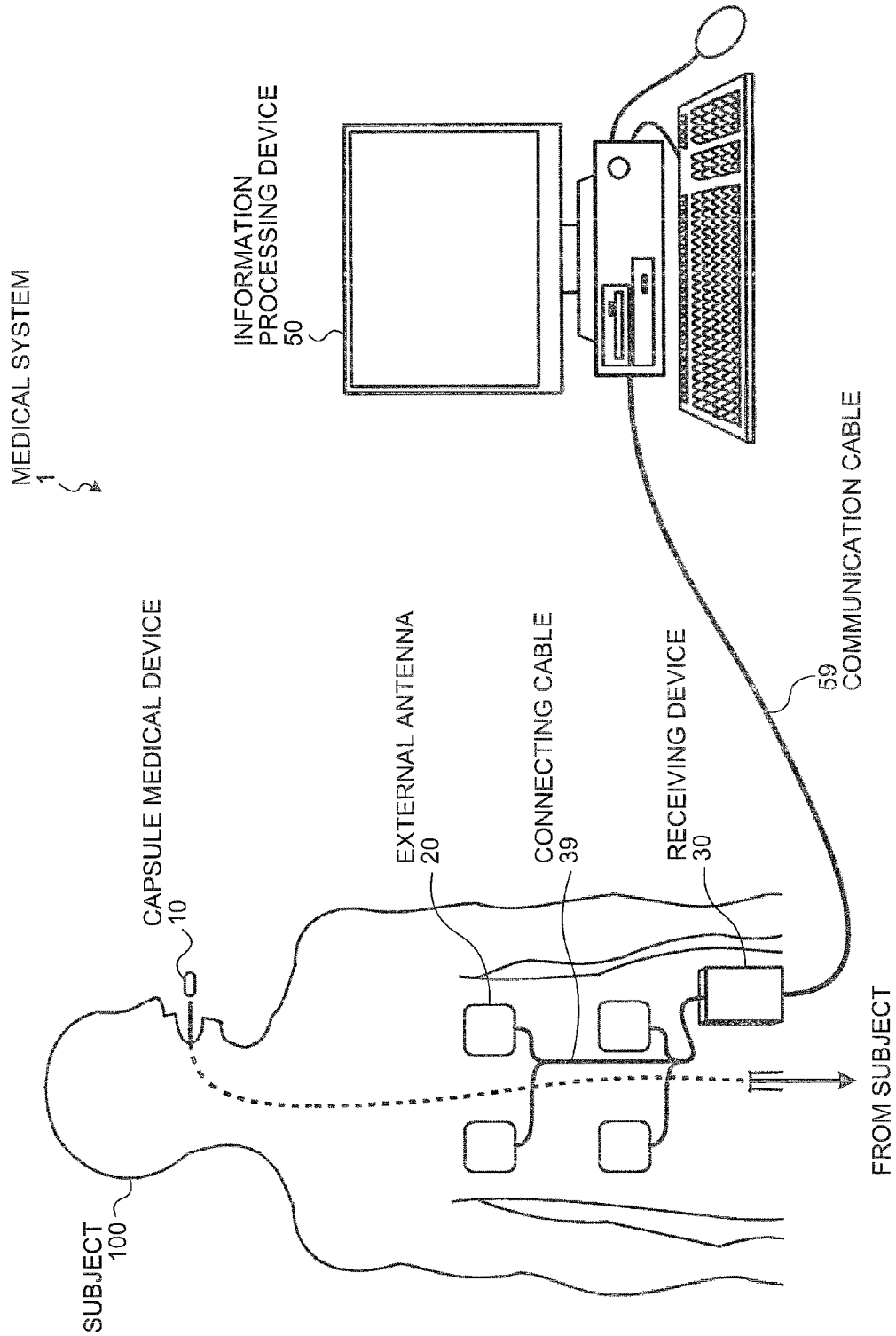
FIG. 1 is a schematic block diagram illustrating the configuration of a medical system according to first to fifth embodiments of the present invention.

FIG. 1 is a schematic block diagram illustrating the configuration of the medical system 1 according to the first embodiment. As illustrated in FIG. 1, the medical system 1 includes the capsule medical device 10 that has the size as small as it can be swallowed by the subject 100, a receiving device 30 that can receive image data transmitted from the capsule medical device 10 as a radio signal, and an information processing device 50 that can communicate with the receiving device 30 via a wired channel or a wireless channel.

An external antenna 20 is connected to the receiving device 30 via a connecting cable 39 or a balun (not illustrated). A radio signal emitted from the capsule medical device 10 is input into the receiving device 30 via the external antenna 20.

The receiving device 30 and the information processing device 50 are connected to each other, for example, via a serial line or a parallel line. In the present embodiment, a USB interface is used for connection between the receiving device 30 and the information processing device 50. In this case, the receiving device 30 is connected to the information processing device 50 by using a USB method. Therefore, in the present embodiment, a USB cable is used as a communication cable 59 illustrated in FIG. 1. However, the present invention is not limited to this. The information processing device 50 and the receiving device 30 can be connected to each other by using various connection modes, such as a small card-type interface for PC (Personal Computer) or Bluetooth®.

As in the present embodiment, when the receiving device 30 is connected to the information processing device 50 by using a USB method, the information processing device 50 is usually a main device (a master) and the receiving device 30 is a sub device (a slave). For this reason, in order that the information processing device 50 acquires image data from the receiving device 30, the information processing device 50 acting as a master requests the receiving device 30 acting as a slave to transmit image data.

For example, the capsule medical device 10 periodically acquires intra-subject images and sequentially transmits the image data to the receiving device 30. Therefore, the information processing device 50 acquires image data from the receiving device 30 and displays the image data periodically and repeatedly. In this way, the information processing device 50 can display intra-subject images to a user in substantially real time. For example, when an image acquisition cycle performed by the capsule medical device 10 is two frames in one second, the information processing device 50 acquires and displays image data from the receiving device 30 in two cycles in at least one second. In this way, the intra-subject images can be displayed in substantially real time. It will be below explained about the details of operations by which the information processing device 50 acquires image data from the receiving device 30.

Figure 2:
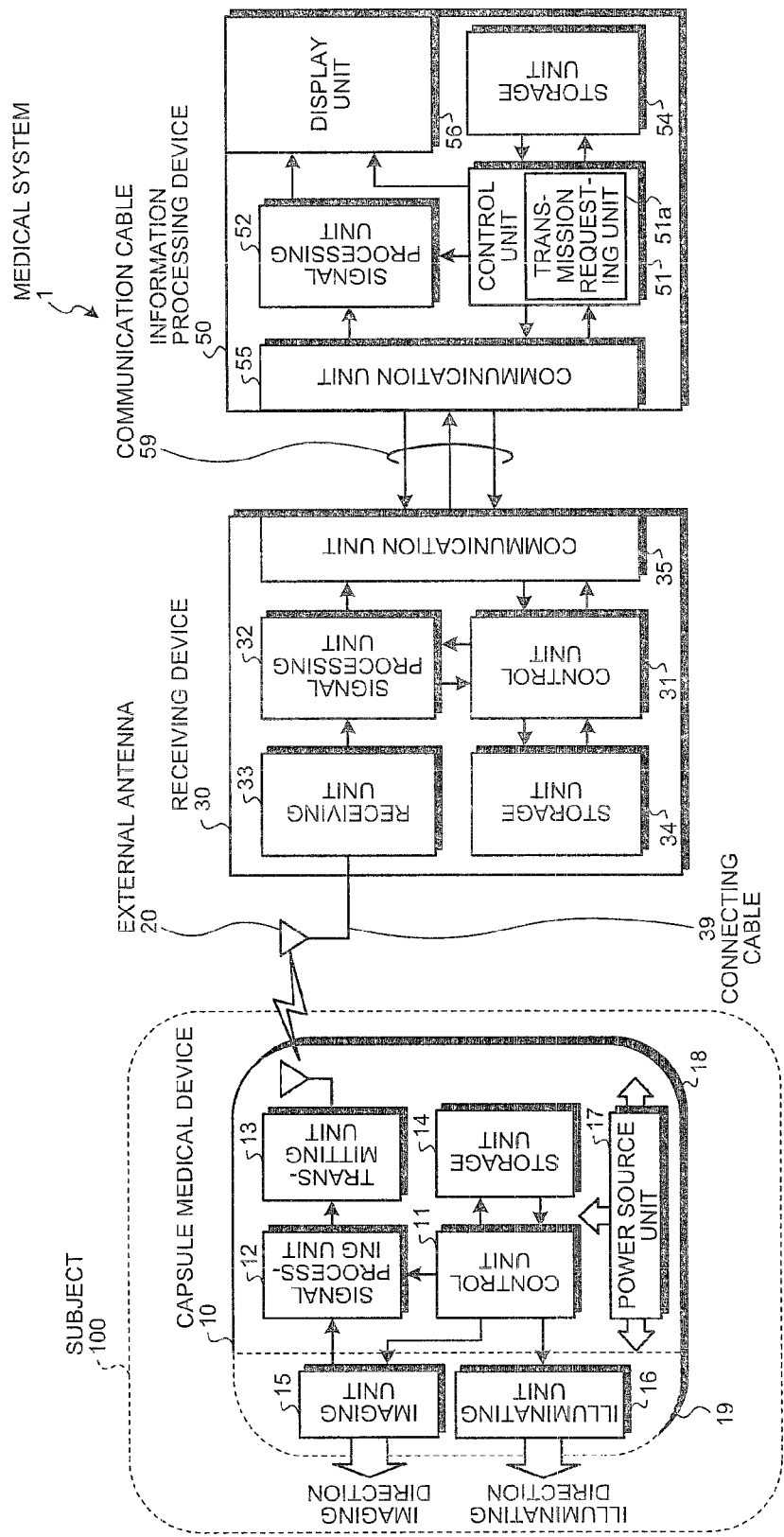
FIG. 2 is a block diagram illustrating the schematic configuration of the medical system according to the first to fifth embodiments of the present invention.

Next, it will be in detail explained about the medical system 1 according to the present embodiment with reference to a block diagram illustrated in FIG. 2. FIG. 2 is a block diagram illustrating the schematic configuration of each device constituting the medical system 1 according to the present embodiment.

As illustrated in FIG. 2, the capsule medical device 10 is introduced into the subject 100 and includes the imaging unit 15, an illuminating unit 16, a signal processing unit 12, a transmitting unit 13, a control unit 11, a storage unit 14, and a power source unit 17. The imaging unit 15 acquires an image for the inside of the subject 100. The illuminating unit 16 illuminates the inside of the subject 100 when the imaging unit 15 captures the inside. The signal processing unit 12 performs a predetermined process on an intra-subject image signal acquired by the imaging unit 15. The transmitting unit 13 transmits image data processed by the signal processing unit 12 to the receiving device 30. The control unit 11 controls each unit included in the capsule medical device 10. The storage unit 14 stores therein various types of programs, various types of setting data, and the like by which the control unit 11 controls each unit. The power source unit 17 supplies power to each unit included in the capsule medical device 10.

The control unit 11 controls each unit in the capsule medical device 10, for example, in accordance with various types of programs and various types of setting data read from the storage unit 14, to make each unit realize various operations such as an operation of capturing the inside of the subject 100 or an operation of transmitting the acquired image data. The control unit 11 can be configured by using an arithmetic processing unit such as a central processing unit (CPU) or a microprocessor (MPU).

The storage unit 14 stores therein various types of programs appropriately executed by the control unit 11 and various types of setting data that are parameters for executing the programs. The storage unit 14 can be configured, for example, by using a read only memory (ROM) and the like. The storage unit 14 can include a random access memory (RAM) that is used by the control unit 11 as an execution area for the various types of programs.

Figure 3:
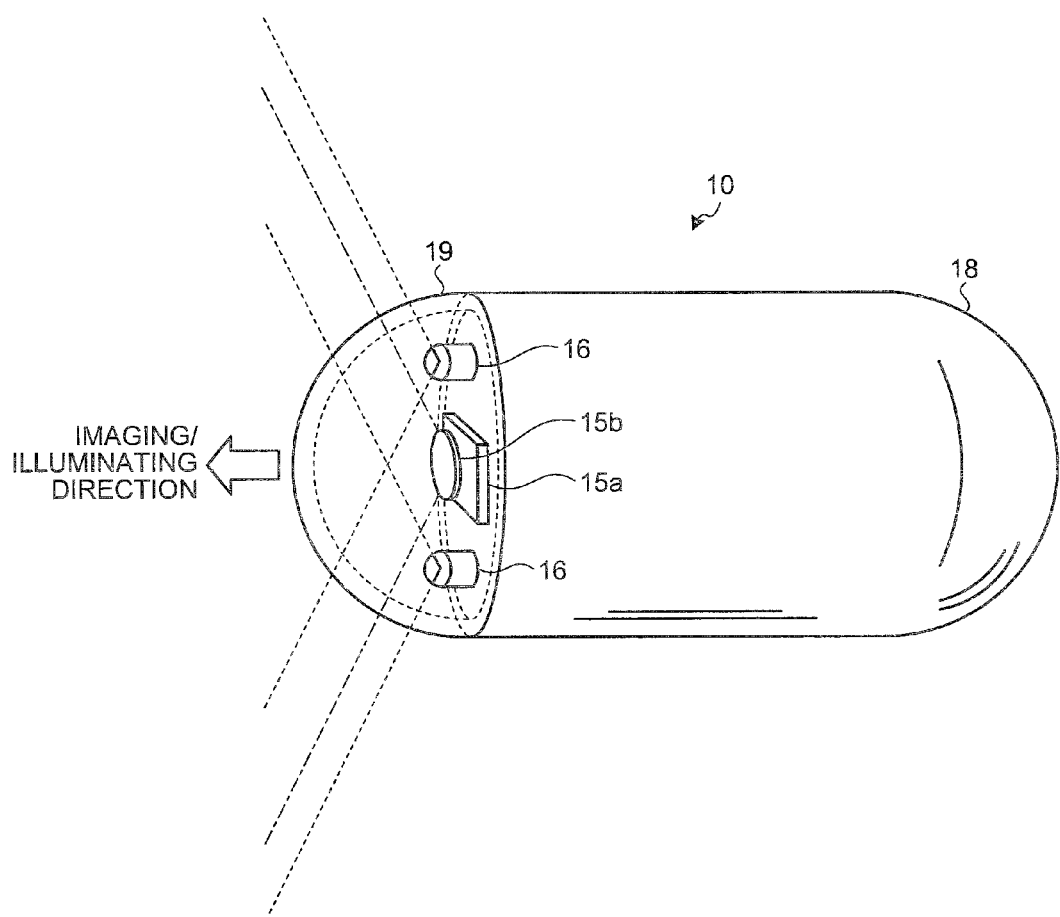
FIG. 3 is an external view illustrating the schematic configuration of a capsule medical device according to the first to fifth embodiments of the present invention.

The imaging unit 15 has, for example, a configuration that an imaging device 15a and an objective lens 15b are mounted on a circuit board (not illustrated) including a drive circuit for driving them (see FIG. 3). The imaging device 15a captures the inside of the subject 100 and generates image data for the inside. The objective lens 15b is arranged at a light receiving surface side of the imaging device 15a. The circuit board mounts thereon the illuminating unit 16 that illuminates the inside of the subject 100 with light during capturing an image and a drive circuit for driving the illuminating unit. The drive circuits of the imaging unit 15 and the illuminating unit 16 are actuated under the control of the control unit 11. In this way, the imaging unit 15 acquires an intra-subject image as image data periodically (for example, two frames in one second) and inputs the data into the signal processing unit 12 located at the subsequent stage. In the following descriptions, it is assumed that the imaging unit 15 and the illuminating unit 16 include the respective drive circuits. Moreover, the imaging unit 15 and the illuminating unit 16 according to the present embodiment are an intra-subject-information acquiring unit that acquires so-called in-vivo information. Therefore, when a temperature, a pressure, a pH value, or the like of the inside of the subject is acquired as the in-vivo information, the imaging unit 15 and the illuminating unit 16 are appropriately replaced by a clinical thermometer, a pressure gage, a pH meter, or the like.

The signal processing unit 12 performs a predetermined process, such as sampling, amplification, or analog to digital conversion, on analog image data input from the imaging unit 15 under the control of the control unit 11, so as to generate digital image data. The image data on which various types of processes are performed are input into the transmitting unit 13.

Under the control of the control unit 11, the transmitting unit 13 performs various processes, such as superposition, modulation, or up-conversion to a reference frequency signal for transmission, on the image data input from the signal processing unit 12. Then, the transmitting unit 13 emits the processed data to the outside of the capsule medical device 10 via an antenna thereof as a radio signal.

As illustrated in FIG. 3, the units of the capsule medical device 10 are accommodated in a capsule-shaped vessel (housing) that includes a substantially cylindrical or semi-elliptic vessel 18 of which one end is a hemispheric dome and the other end is opened and a hemispheric cap 19 that seals the inside of the vessel 18 by fitting in the opening of the vessel 18. The capsule-shaped vessel (18 and 19) has, for example, the size as small as it can be swallowed by the subject 100. In the present embodiment, at least the cap 19 is formed of transparent materials. The imaging unit 15 and the illuminating unit 16 described above are arranged at the cap 19 side in the capsule-shaped vessel (18 and 19). The imaging direction of the imaging unit 15 and the illuminating direction of the illuminating unit 16 are directed to the outside of the capsule medical device 10 via the cap 19 as illustrated in FIGS. 2 and 3. In this way, the imaging unit 15 can capture images for the inside of the subject 100 while the illuminating unit 16 illuminates the inside of the subject 100.

In the present embodiment, the capsule medical device 10 has one imaging unit as an example. However, the present invention is not limited to this. For example, the present invention has a configuration that transparent caps are attached to both ends of the vessel 18 in a longitudinal direction. In this case, the capsule medical device 10 can include a plurality of imaging units and/or illuminating units by providing the imaging unit and the illuminating unit at the both ends.

Next, it will be in detail explained about the configuration of the receiving device 30 according to the present embodiment with reference to FIG. 2. As illustrated in FIG. 2, the receiving device 30 is arranged at the outside (for example, the surface of the subject 100, the clothes of the subject 100, and the like) of the subject 100, and includes a receiving unit 33, a signal processing unit 32, a control unit 31, a storage unit 34, and a communication unit 35. The receiving unit 33 receives the image data transmitted from the capsule medical device 10. The signal processing unit 32 performs a predetermined process on the received image data. The control unit 31 controls each unit included in the receiving device 30. The storage unit 34 stores therein various types of programs and various types of setting data by which the control unit 31 controls each unit. The communication unit 35 functions as an interface that communicates with the information processing device 50 to be described below.

The control unit 31 controls each unit included in the receiving device 30, for example, in accordance with various types of programs and various types of setting data read from the storage unit 34, in order to make each unit realize various operations such as an operation of transferring the image data acquired from the capsule medical device 10 to the information processing device 50. The control unit 31 can be configured by using an arithmetic processing unit such as CPU or MPU.

The storage unit 34 stores therein various types of programs appropriately executed by the control unit 31 and various types of setting data that are parameters to be used for executing the programs. The storage unit 34 can be configured, for example, by using ROM or RAM. Moreover, the storage unit 34 can function as an execution area when the control unit 31 executes the various types of programs.

The receiving unit 33 performs, under the control of the control unit 31, various processes such as filtering, down-conversion, demodulation, and decryption on the received signal received from the capsule medical device 10 via the external antenna 20. After that, the receiving unit 33 inputs the processed signal to the signal processing unit 32.

The signal processing unit 32 separates image data from the data signal input from the receiving unit 33 and reconfigures the image data under the control of the control unit 31. After that, the signal processing unit 32 inputs the reconfigured image data to the communication unit 35.

The communication unit 35 establishes, under the control of the control unit 31, the communication with a communication unit 55 of the information processing device 50, in order to intermediate between the receiving device 30 and the information processing device 50 to transmit and receive various types of data signals such as image data or request and response signals. The communication unit 35 is configured, for example, by using a USB interface. Therefore, the communication cable 59 such as a USB cable is connected to the communication unit 35. In the present embodiment, the communication unit 35 further has a function that functions as a power dispatching unit that distributes an electric power supplied from the information processing device 50 to the units of the receiving device 30. Therefore, the receiving device 30 according to the present embodiment can be positioned as a peripheral device that operates by using an electric power (USB bus power) supplied from the information processing device 50 via the USB cable.

The receiving device 30 according to the present embodiment receives image data periodically transmitted from the capsule medical device 10 and transmits the image data to the information processing device 50 in response to the transmission request of the information processing device 50. However, the present invention is not limited to this. For example, the receiving device 30 can receive operator guidance for the capsule medical device 10, which is input into the information processing device 50 or another operation terminal, and transmit the guidance to the capsule medical device 10. In this case, the transmission request is a request signal of requesting the transmission of image data.

Next, it will be in detail explained about the configuration of the information processing device 50 according to the present embodiment with reference to FIG. 2. The information processing device 50 according to the present embodiment is an information processing device including a calculation function and a display function, such as a personal computer. As illustrated in FIG. 2, the information processing device 50 includes the communication unit 55, a signal processing unit 52, a display unit 56, a control unit 51, and a storage unit 54. The communication unit 55 functions as an interface that communicates with the receiving device 30. The signal processing unit 52 performs a predetermined process on image data input via the communication unit 55 and generates an image signal for display. The display unit 56 displays an intra-subject image based on the image signal input from the signal processing unit 52. The control unit 51 controls each unit included in the information processing device 50 and executes various types of operations. The storage unit 54 stores therein programs in which various operations executed by the control unit 51 are described and various types of setting data.

For example, the control unit 51 executes various control actions, arithmetic processing, and the like in accordance with various types of programs and various types of setting data read from the storage unit 54. The control unit 51 can be configured by using an arithmetic processing unit such as CPU.

The control unit 51 includes a transmission requesting unit 51a that generates a transmission request of requesting the receiving device 30 to transmit the image data and inputs the transmission request into the communication unit 55. The transmission requesting unit 51a is realized, for example, by executing a predetermined program read from the storage unit 54. The execution of the program is performed by the control unit 51. It will be below explained about detailed operations of the transmission requesting unit 51a.

The storage unit 54 stores therein various types of programs appropriately executed by the control unit 51 and various types of setting data that are parameters to be used for executing the programs. The storage unit 54 can be configured, for example, by using ROM or RAM. Moreover, the storage unit 54 can function as an execution area when the control unit 51 executes the various types of programs.

The communication unit 55 establishes, under the control of the control unit 51, the communication with the communication unit 35 of the receiving device 30, in order to intermediate between the receiving device 30 and the information processing device 50 to transmit and receive various types of data signals such as image data or request and response signals. The communication unit 55 is configured, for example, by using a USB interface. Therefore, the communication cable 59 such as a USB cable is connected to the communication unit 55. In the present embodiment, the communication unit 55 further has a function of supplying an electric power to the receiving device 30 via the communication cable 59. In this case, the connection between the receiving device 30 and the information processing device 50 is not limited to a wired connection. The connection can be a wireless connection. As an example of wireless connection, there are WLAN, Wireless USB, BlueTooth®, and the like. In other words, the connection between the receiving device 30 and the information processing device 50 can be any of wired and wireless connections. This is similar to the connection in the following embodiments.

The signal processing unit 52 is configured by using a video chip and a video memory that are mounted on a so-called video card or the like. The signal processing unit 52 generates a screen signal for display and a synchronizing signal from image data and the like input from the communication unit 55 or the control unit 51, and sequentially outputs the signals to the display unit 56.

The display unit 56 is configured by using a display such as a liquid crystal display (LCD), a cathode ray tube (CRT) display, or an organic electro-luminescence (EL) display. The display unit 56 displays an image such as an intra-subject image to the user based on the screen signal and the synchronizing signal input from the signal processing unit 52.

Next, it will be in detail explained about operations of the medical system 1 according to the present embodiment with reference to the drawings. As described above, in the medical system 1, the capsule medical device 10 periodically captures images for the inside of the subject 100 by using the imaging unit 15 and the illuminating unit 16 driven by the control unit 11 to generate image data of intra-subject images, and transmits the image data to the receiving device 30 by using the transmitting unit 13.

On the contrary, the receiving device 30 performs a predetermined process on the image data received via the external antenna 20 and the receiving unit 33 by using the signal processing unit 32, and then stores the processed data in the storage unit 34. After that, when the transmission request for image data is received from the information processing device 50 via the communication unit 35, the image data stored in the storage unit 34 is read by the control unit 31 and is transmitted to the information processing device 50 via the communication unit 55. In this way, the image data acquired by the capsule medical device 10 is input into the information processing device 50.

Figure 4:
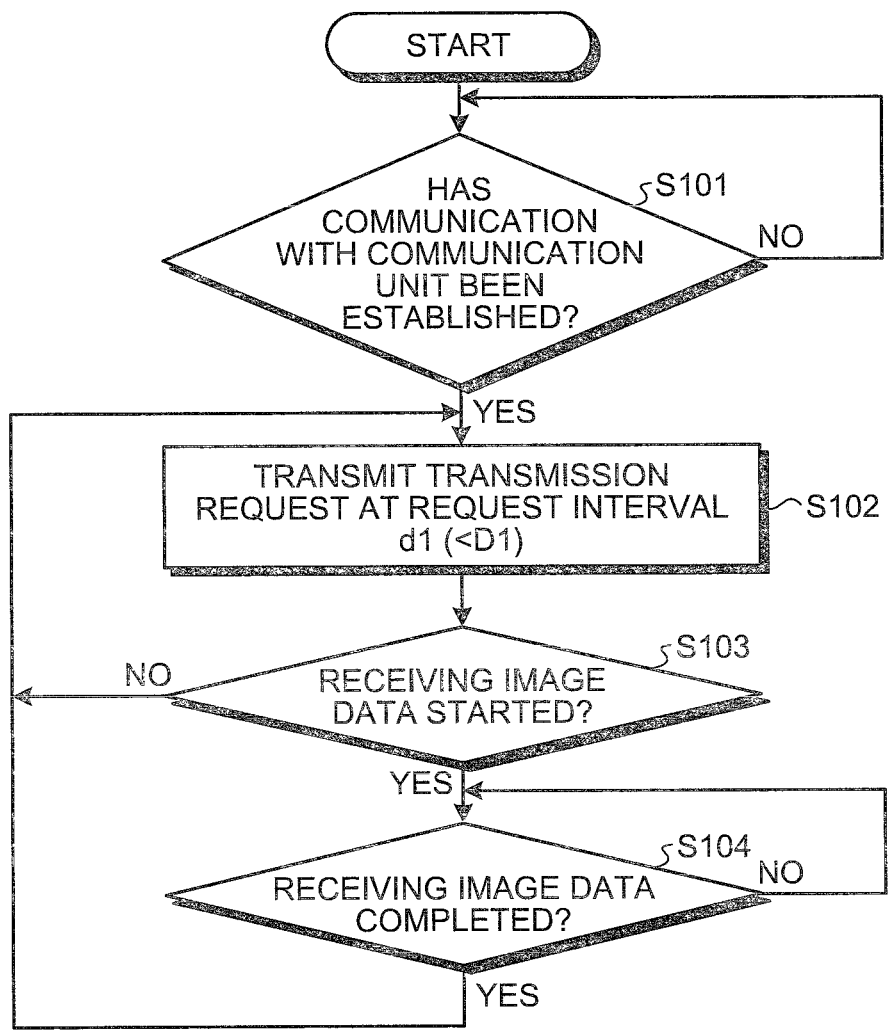
FIG. 4 is a flowchart illustrating operations performed by a transmission requesting unit in an information processing device according to the first embodiment of the present invention.
Figure 5:
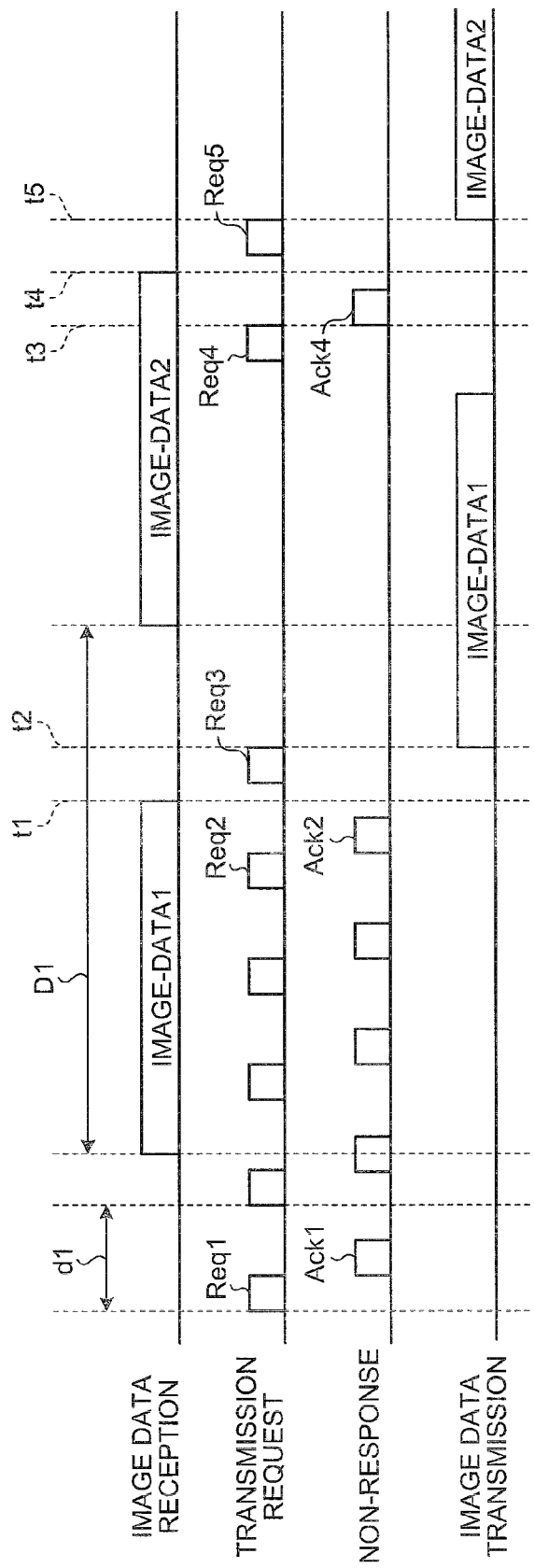
FIG. 5 is a timing chart of data that is transmitted and received between a receiving device and the information processing device according to the first embodiment of the present invention.

Next, it will be explained about detailed operations when the information processing device 50 acquires image data from the receiving device 30 with reference to FIGS. 4 and 5. FIG. 4 is a flowchart illustrating operations of the transmission requesting unit 51a in the information processing device 50 according to the present embodiment. FIG. 5 is a timing chart of data that is transmitted and received between the receiving device 30 and the information processing device 50. The operation illustrated in FIG. 4 is terminated by interrupt handling performed by the control unit 51, for example, when the control unit 51 detects that communication between the receiving device 30 and the information processing device 50 is cut off.

As illustrated in FIG. 4, the transmission requesting unit 51a, which is executed in the control unit 51 of the information processing device 50, waits until the communication unit 55 establishes communication with the communication unit 35 of the receiving device 30 (Step S101: No). When the communication is established (Step S101: Yes), the transmission requesting unit 51a first transmits transmission requests to the receiving device 30 via the communication unit 55 at a certain time interval (request interval d1) (Step S102). As illustrated in FIG. 5, the request interval d1 is set to a time interval (d1<D1) sufficiently smaller than an acquisition interval (imaging interval D1) of an intra-subject image in the capsule medical device 10. For example, when the imaging interval D1 is 0.5 seconds, the request interval d1 is set to 0.1 seconds or less. By setting the request interval d1 to a value sufficiently smaller than the imaging interval D1, an intra-subject image captured by the capsule medical device 10 can be displayed on the display unit 56 in substantially real time. In this case, the management of the request interval d1 can be realized, for example, by counting clocks (not illustrated) generated in the information processing device 50 by means of a soft counter executed in the control unit 51.

The transmission of periodical transmission request in Step S102 is continued until image data is transmitted from the receiving device 30 in response to the transmission request (Step S103: No). In this case, the present embodiment has a configuration that the control unit 31 of the receiving device 30 makes the storage unit 34 once store the image data received from the capsule medical device 10 and then receives the transmission request received from the information processing device 50. As illustrated in FIG. 5, image data to be transmitted is not present for transmission requests Req1 and Req2, which are input into the control unit 31 before a timing t1 at which image-data1 is completely stored in the storage unit 34, among the transmission requests transmitted from the transmission requesting unit 51a to the receiving device 30. Therefore, the control unit 31 of the receiving device 30 transmits response signals (non-responses Ack1 and Ack2) indicating that image data cannot be transmitted to the information processing device 50. On the other hand, image data to be transmitted is present for a transmission request Req3 that is input into the control unit 31 after the image-data1 is completely stored in the storage unit 34, for example, at the time of a timing t2. Therefore, the control unit 31 reads the image-data1 stored in the storage unit 34 in response to the transmission request Req3 and transmits the data to the information processing device 50.

At this time, the image data that is read from the storage unit 34 and is transmitted to the information processing device 50 can be erased from the storage unit 34. Meanwhile, when a plurality of image data that is not yet transmitted is stored in the storage unit 34 for some reason, the control unit 31 can control to sequentially read image data from old image data and transmit the read old image data to the information processing device 50. Alternatively, the control unit 31 can control to read only the latest image data to transmit the latest image data to the information processing device 50 and erase the other image data.

As described above, in the present embodiment, the control unit 31 determines whether image data is transmitted by using a time, at which the image data received from the capsule medical device 10 is completely stored in the storage unit 34, as a standard. However, the present invention is not limited to this. For example, when there is image data that is being received from the capsule medical device 10, the control unit 31 can determine that the image data can be transmitted. When such a configuration is employed, the control unit 31 can directly transmit image data that is being received from the capsule medical device 10 to the information processing device 50 without storing the image data in the storage unit 34.

When the reception of image data transmitted from the receiving device 30 as described above is started (Step S103: Yes), the transmission requesting unit 51a waits until the reception of image data is completed (Step S104: No). After that, when the reception of image data is completed (Step S104: Yes), the transmission requesting unit 51a returns the control to Step S102 and again transmits the transmission request to the receiving device 30 at the request interval d1 having a time interval smaller than the imaging interval D1. In this way, as illustrated in FIG. 5, the control unit 31 of the receiving device 30 transmits a non-response Ack4 with respect to a transmission request Req4 that is input at a timing t3 before a timing t4 at which image-data2 that is next image data is completely stored in the storage unit 34 in the receiving device 30. Then, the control unit 31 reads the image-data2 from the storage unit 34 with respect to a request signal Req5 that is input at a timing t5 after the timing t4 and transmits the image-data2 to the information processing device 50. After that, the transmission requesting unit 51a repeats similar operations until a termination instruction is input by interrupt handling, for example.

By operating as above, in the present embodiment, the information processing device 50 transmits the transmission requests at a first time interval (request interval d1) smaller than a predetermined time interval (imaging interval D1) at which the capsule medical device 10 transmits intra-subject images, from the communication establishment with the receiving device 30 connected as a slave to the reception of image data. Therefore, the information processing device 50 can specify a timing, at which the receiving device 30 can transmit the image data, by a simple procedure and can acquire the image data in substantially real time. In this way, the information processing device 50 can display the image data for the intra-subject images acquired by the capsule medical device 10 to the user in substantially real time. Moreover, because the information processing device 50 does not transmit the transmission request during receiving the image data, information exchanged between the receiving device 30 and the information processing device 50 can be reduced. In this manner, according to the present embodiment, intra-subject images that are in-vivo information acquired by the capsule medical device 10 can be displayed to the user in substantially real time by simple procedures and little communications traffic.

Figure 6:
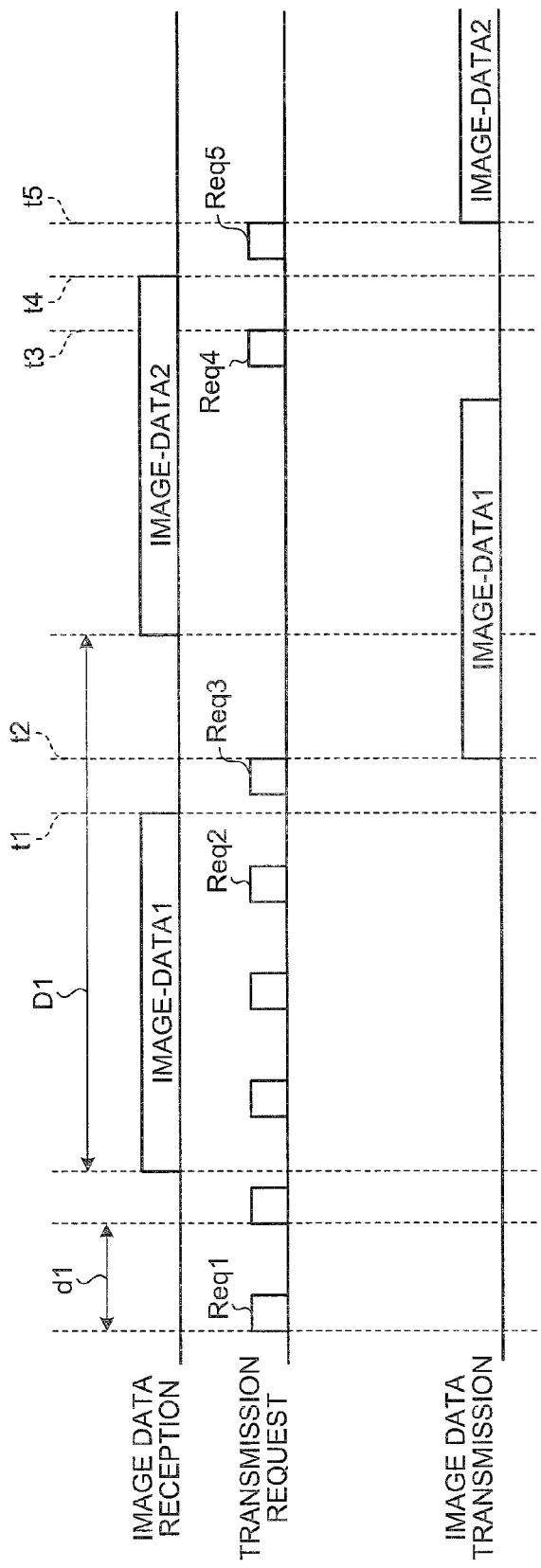
FIG. 6 is a timing chart of data that is transmitted and received between the receiving device and the information processing device according to an alternative example of the first embodiment of the present invention.

In the present embodiment, the control unit 31 of the receiving device 30 transmits the non-response (see FIG. 5) to the information processing device 50 when the control unit 31 cannot transmit image data. However, the present invention is not limited to this. For example, as illustrated in an alternative example of FIG. 6, the control unit 31 may not transmit the non-response when image data to be transmitted is not present. In this case, the control unit 31 cancels the input transmission request. By operating as above, an amount of signal transmitted and received between the receiving device 30 and the information processing device 50 can be reduced.

Second Embodiment

Next, it will be in detail explained about the configuration and operation of a medical system according to the second embodiment of the present invention with reference to the drawings. In addition, for simplification of explanation about the configuration or operation similar to that of the first embodiment of the present invention, the detailed description is omitted by putting the same symbols.

The medical system according to the second embodiment can have the configuration similar to that of the medical system 1 that is exemplified in the first embodiment of the present invention. However, in the second embodiment, procedures by which the information processing device 50 acquires image data from the receiving device 30 are different from those in the first embodiment.

In the second embodiment, the time interval (imaging interval D1) at which the capsule medical device 10 acquires intra-subject images is previously determined. Therefore, in the present embodiment, the transmission requesting unit 51a, which is executed in the control unit 51 of the information processing device 50, operates to transmit a transmission request to the receiving device 30 at the same time interval (request interval d2) as the imaging interval D1 after receiving initial image data. By operating as above, an amount of signal transmitted and received between the receiving device 30 and the information processing device 50 can be reduced.

Next, it will be explained about procedures by which the information processing device 50 acquires image data from the receiving device 30 in consideration of an operation of the transmission requesting unit 51a of the information processing device 50 and a timing chart of data transmitted and received between the receiving device 30 and the information processing device 50.

Figure 7:
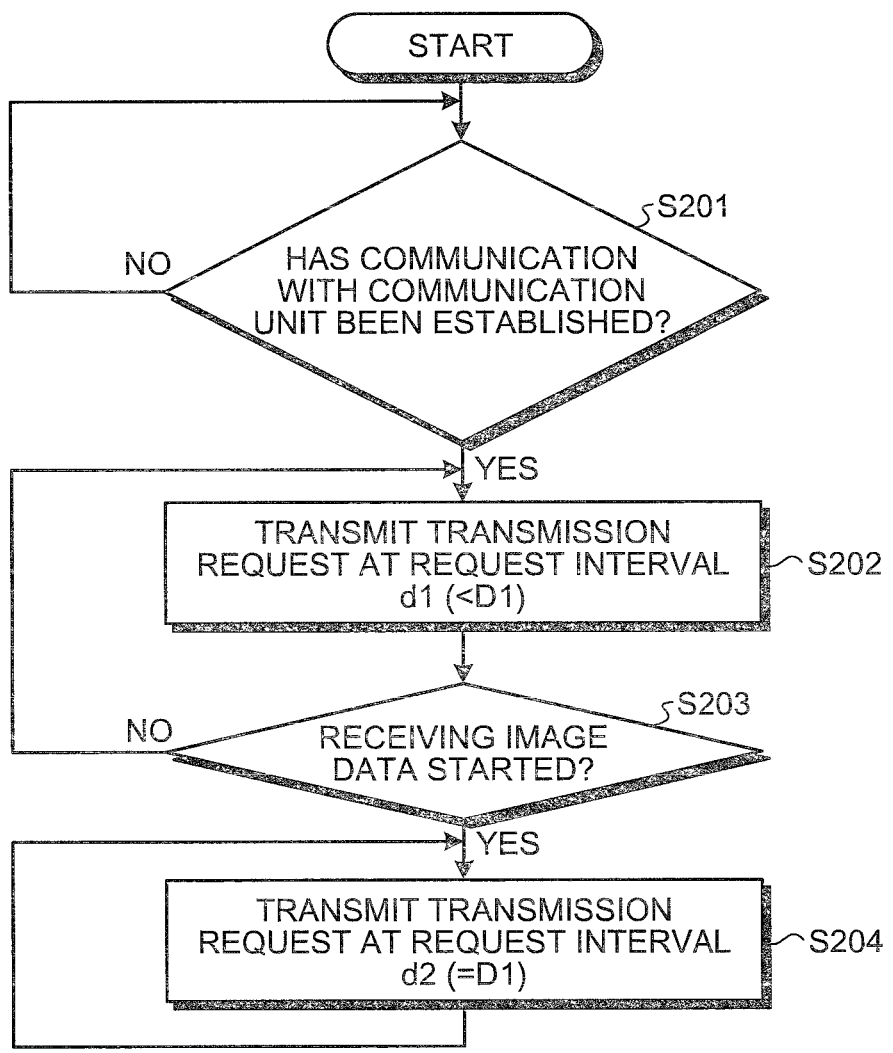
FIG. 7 is a flowchart illustrating operations performed by the transmission requesting unit in the information processing device according to the second embodiment of the present invention.
Figure 8:
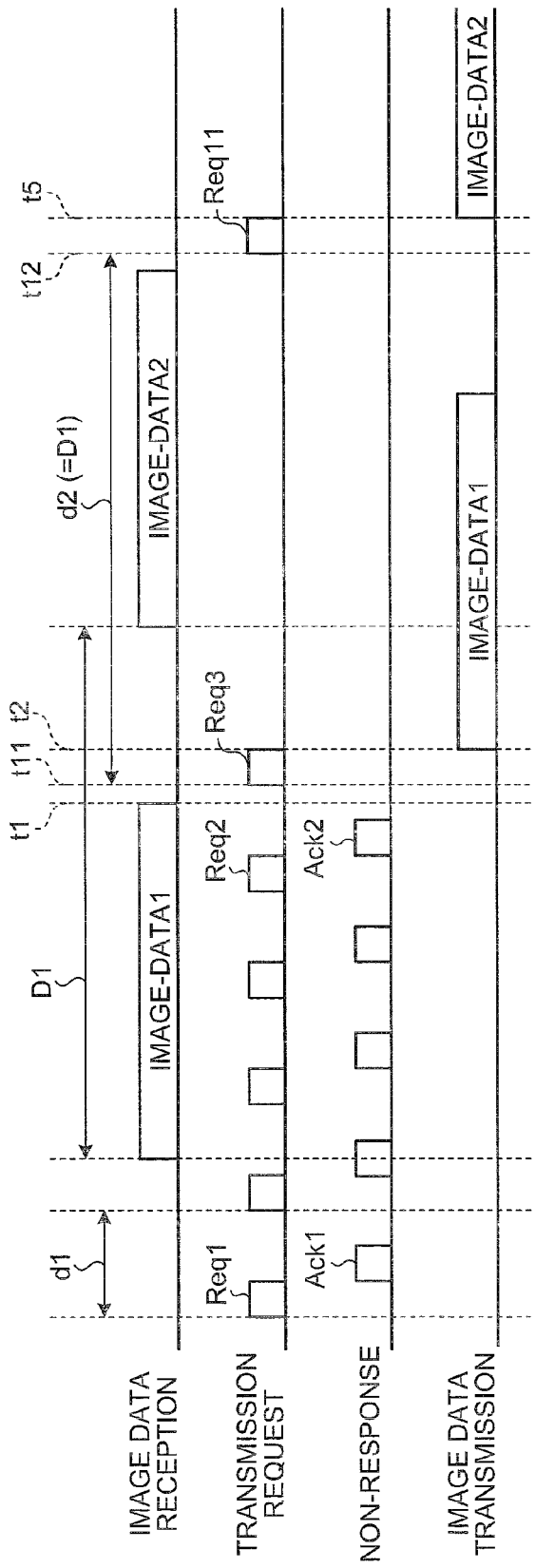
FIG. 8 is a timing chart of data that is transmitted and received between the receiving device and the information processing device according to the second embodiment of the present invention.

FIG. 7 is a flowchart illustrating the operation of the transmission requesting unit 51a in the information processing device 50 according to the second embodiment. FIG. 8 is a timing chart of data that is transmitted and received between the receiving device 30 and the information processing device 50. The operation illustrated in FIG. 7 is terminated by interrupt handling performed by the control unit 51, for example, when the control unit 51 detects that communication between the receiving device 30 and the information processing device 50 is cut off.

As illustrated in FIG. 7, the transmission requesting unit 51a, which is executed in the control unit 51 of the information processing device 50, waits until the communication unit 55 establishes communication with the communication unit 35 of the receiving device 30 (Step S201: No). When the communication is established (Step S201: Yes), the transmission requesting unit 51a transmits transmission requests to the receiving device 30 via the communication unit 55 at a constant request interval d1 similarly to Step S102 of FIG. 4 (Step S202). In this case, the transmission of the transmission request in Step S202 is continued until image data is transmitted from the receiving device 30 in response to the transmission request (Step S203: No).

When the reception of image data transmitted from the receiving device 30 is started in response to the transmission request of Step S202 (Step S203: Yes), the transmission requesting unit 51a transmits a transmission request to the receiving device 30 via the communication unit 55 at a timing obtained by adding the same time (request interval d2) as the imaging interval D1 to the timing at which the previous transmission request is transmitted (Step S204). For example, as illustrated in FIG. 8, the transmission requesting unit 51a transmits the next transmission request Req11 to the receiving device 30 at a timing t12 obtained by adding the request interval d2 to a timing t11 at which the transmission request Req3 is finally transmitted in Step S202. After that, the transmission requesting unit 51a returns the control to Step S204 and then repeats to transmit the transmission request at the request interval d2.

In the present embodiment, the transmission requests are transmitted at the first time interval (request interval d1) smaller than the predetermined time interval (imaging interval D1) at which the capsule medical device 10 transmits intra-subject images, from the communication establishment with the receiving device 30 connected as a slave to the reception of at least one image data. Therefore, the timing at which the receiving device 30 can first transmit image data can be specified by a simple procedure. Moreover, after at least one image data is received, the transmission requests are transmitted at a second time interval (request interval d2) larger than the first time interval (request interval d1). Therefore, information exchanged between the receiving device 30 and the information processing device 50 can be reduced after at least one image data is received. Furthermore, image data are acquired and displayed at the second time interval (request interval d2) equal to the imaging interval D1. Therefore, image data for intra-subject images acquired by the capsule medical device 10 can be displayed to the user in substantially real time. In this manner, according to the present embodiment, intra-subject images that are in-vivo information acquired by the capsule medical device 10 can be displayed to the user in substantially real time by simple procedures and little communications traffic.

Figure 9:
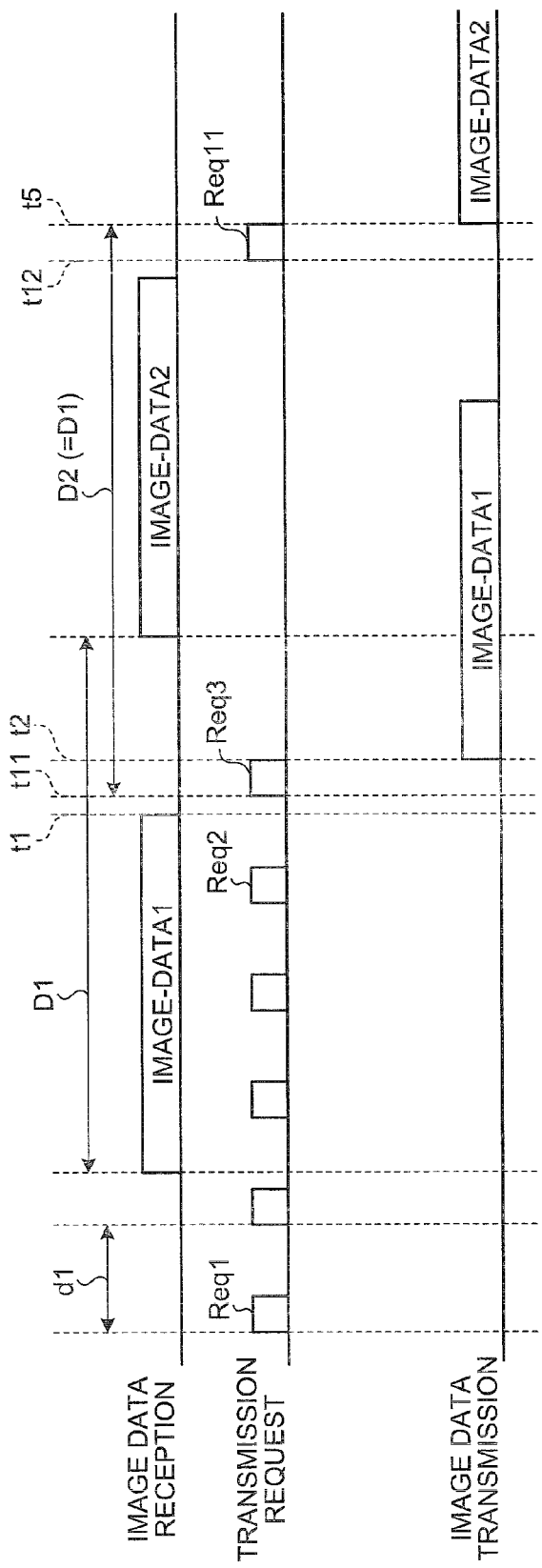
FIG. 9 is a timing chart of data that is transmitted and received between the receiving device and the information processing device according to an alternative example of the second embodiment of the present invention.

In the present embodiment, similarly to the first embodiment of the present invention, the control unit 31 of the receiving device 30 transmits the non-response (see FIG. 8) to the information processing device 50 when the control unit 31 cannot transmit image data. However, the present invention is not limited to this. For example, as illustrated in an alternative example of FIG. 9, the control unit 31 may not transmit the non-response when image data to be transmitted is not present. In this case, the control unit 31 cancels the input transmission request. By operating as above, an amount of signal transmitted and received between the receiving device 30 and the information processing device 50 can be reduced.

Third Embodiment

Next, it will be in detail explained about the configuration and operation of a medical system according to the third embodiment of the present invention with reference to the drawings. In addition, for simplification of explanation about the configuration or operation similar to that of the first or second embodiment of the present invention, the detailed description is omitted by putting the same symbols.

The medical system according to the third embodiment can have the configuration similar to that of the medical system 1 that is exemplified in the first embodiment of the present invention. However, in the third embodiment, procedures by which the information processing device 50 acquires image data from the receiving device 30 are different from those in the first or second embodiment.

In the third embodiment, the time interval (imaging interval D1) at which the capsule medical device 10 acquires intra-subject images is not previously determined. Therefore, in the present embodiment, the information processing device 50 computes the imaging interval D1 from time stamps added to image data and sets the imaging interval as the request interval d2.

A time stamp is time information. For example, the time stamp can be added to image data by the control unit 11 when the capsule medical device 10 acquires the image data. Alternatively, the time stamp can be added to image data by the control unit 31 when the receiving device 30 receives the image data from the capsule medical device 10 or stores the received image data in the storage unit 34.

Next, it will be explained about procedures by which the information processing device 50 acquires image data from the receiving device 30 in consideration of an operation of the transmission requesting unit 51a of the information processing device 50 and a timing chart of data transmitted and received between the receiving device 30 and the information processing device 50.

Figure 10:
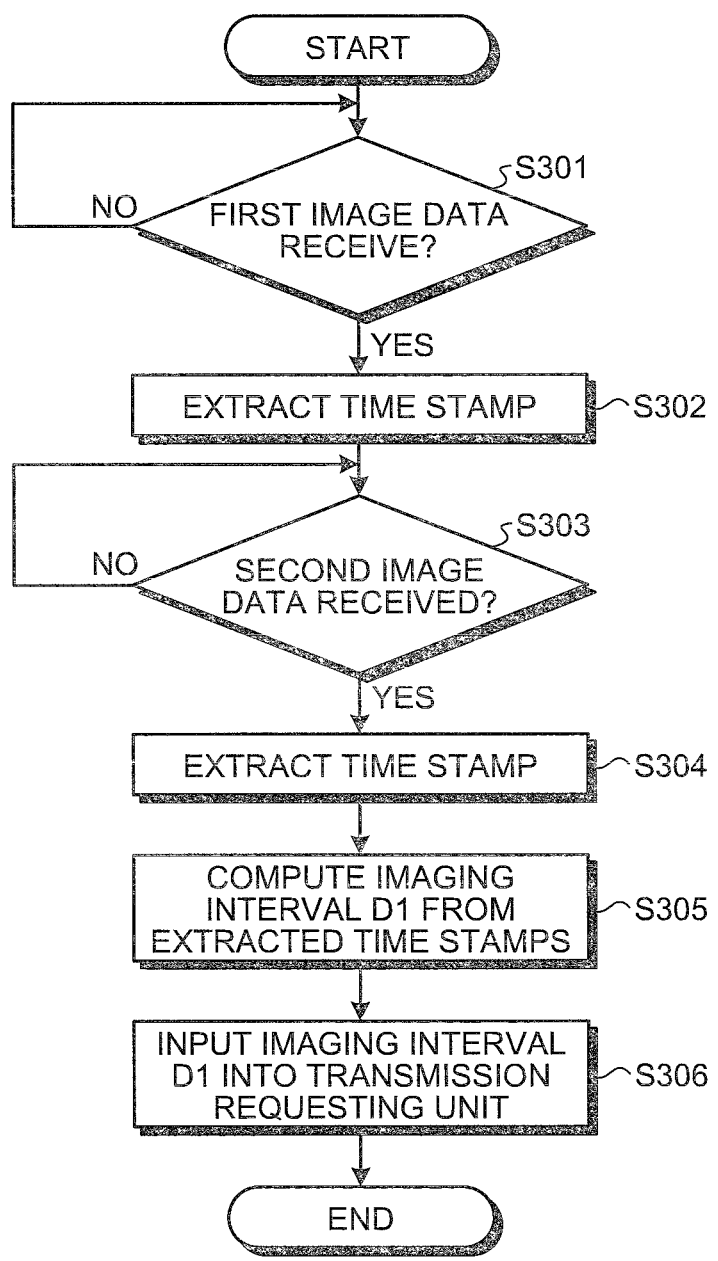
FIG. 10 is a flowchart illustrating operations for computing a request interval d2 from a time stamp in a control unit of the information processing device according to the third embodiment of the present invention.
Figure 11:
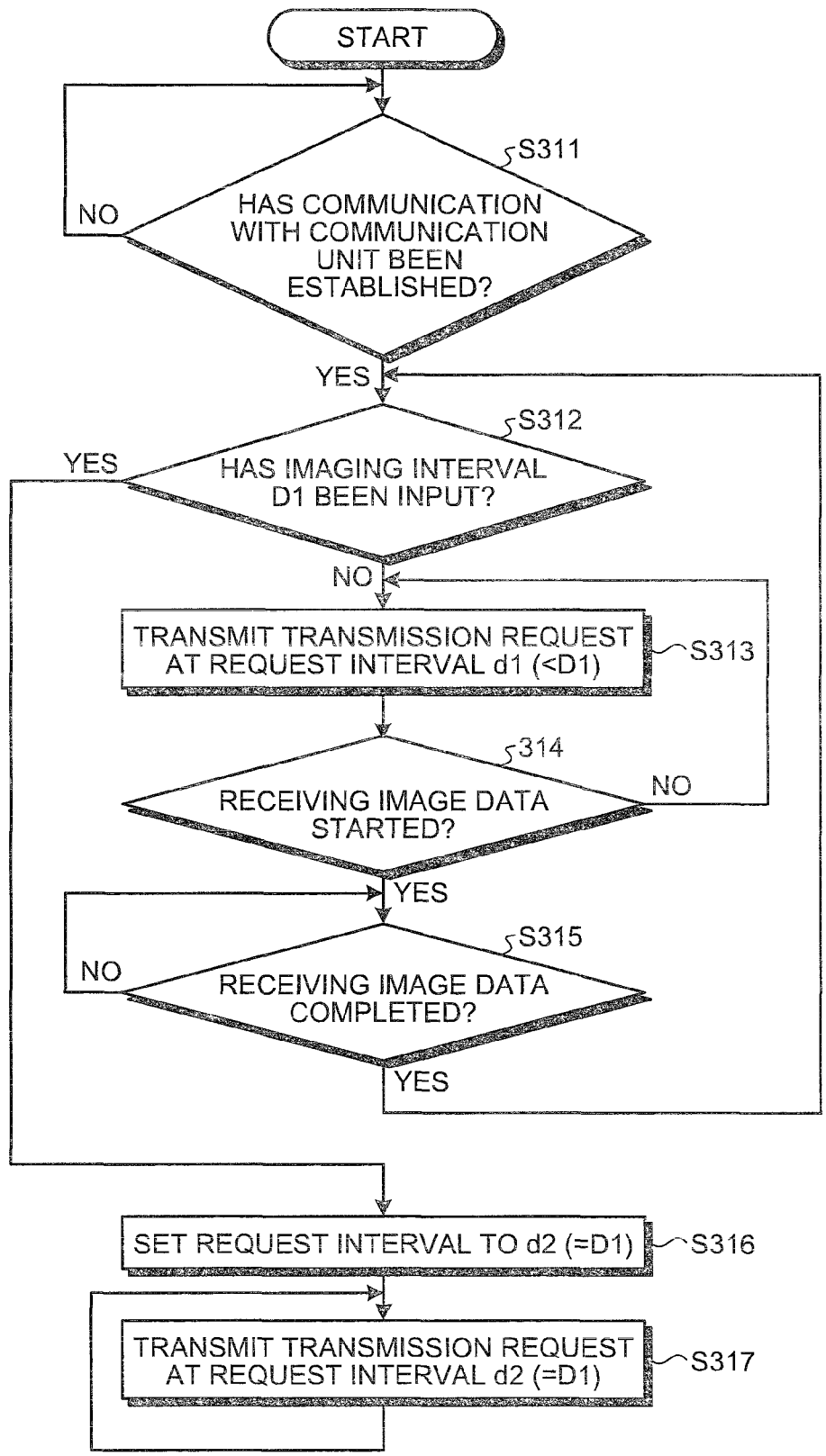
FIG. 11 is a flowchart illustrating operations performed by the transmission requesting unit in the information processing device according to the third embodiment of the present invention.
Figure 12:
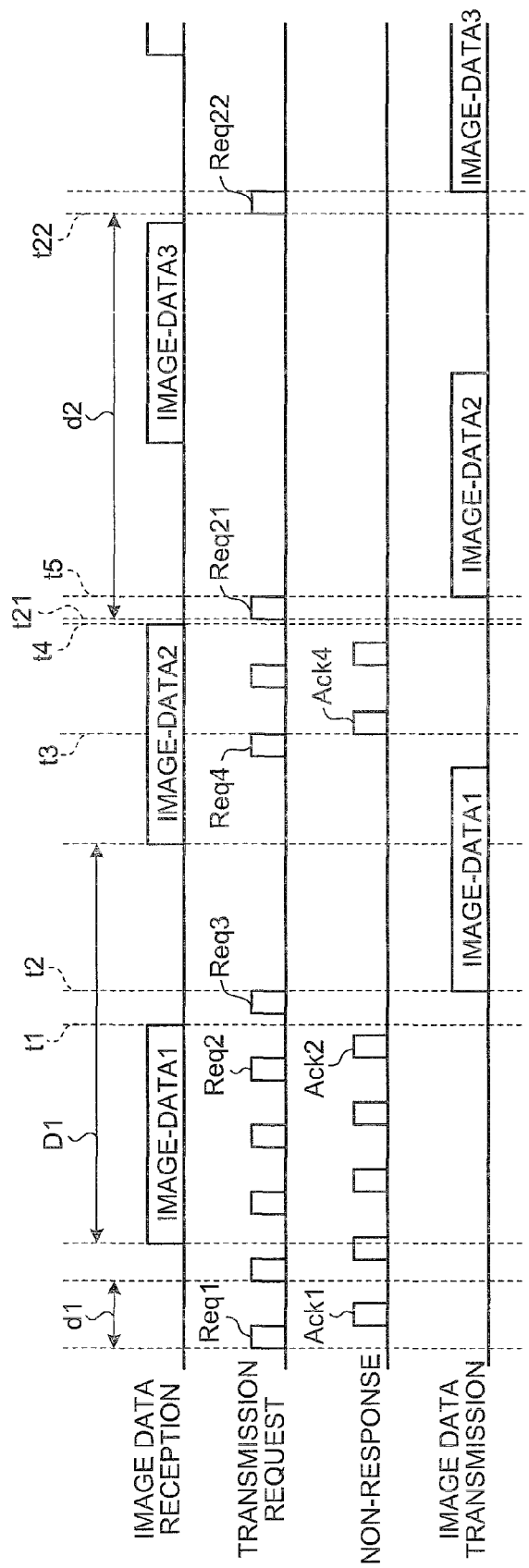
FIG. 12 is a timing chart of data that is transmitted and received between the receiving device and the information processing device according to the third embodiment of the present invention.

FIG. 10 is a flowchart illustrating operations when the control unit 51 of the information processing device 50 according to the third embodiment computes the request interval d2 from time stamps. FIG. 11 is a flowchart illustrating operations of the transmission requesting unit 51a of the information processing device 50 according to the third embodiment. FIG. 12 is a timing chart of data that is transmitted and received between the receiving device 30 and the information processing device 50. The operation illustrated in FIG. 11 is terminated by interrupt handling performed by the control unit 51, for example, when the control unit 51 detects that communication between the receiving device 30 and the information processing device 50 is cut off.

As illustrated in FIG. 10, when computing the request interval d2, the control unit 51 of the information processing device 50 determines whether a first image data is received from the receiving device 30 (Step S301). When the first image data is received (Step S301: Yes), the control unit 51 extracts an added time stamp from the image data (Step S302). In this case, the determination of Step S301 is repeated until the first image data is received (Step S301: No).

Next, the control unit 51 determines whether a second image data is received from the receiving device 30 (Step S303). When the second image data is received (Step S303: Yes), the control unit 51 extracts an added time stamp from the image data (Step S304). In this case, the determination of Step S303 is repeated until the second image data is received (Step S303).

When time stamps added to two image data are respectively extracted in this manner, the control unit 51 computes the imaging interval D1 in the capsule medical device 10 from the two time stamps (Step S305). The imaging interval can be calculated, for example, by subtracting the time indicated by the time stamp added to the first image data from the time indicated by the time stamp added to the second image data. Moreover, times from the image data acquisition of the capsule medical device 10 to the reception of the receiving device 30 or the storage of the storage unit 34 are substantially the same. Therefore, the imaging interval D1 can be computed by subtracting the time indicated by the time stamp added to the first image data from the time indicated by the time stamp added to the second image data even if the receiving device 30 adds time stamps to image data.

In this way, when the imaging interval D1 is computed, the control unit 51 inputs the computed imaging interval D1 into the transmission requesting unit 51a (Step S306), and then terminates the process.

By operating as above, the imaging interval D1 can be calculated even when the imaging interval D1 is not determined in the information processing device 50.

On the other hand, as illustrated in FIG. 11, the transmission requesting unit 51a, which is executed in the control unit 51 of the information processing device 50, waits until the communication unit 55 establishes communication with the communication unit 35 of the receiving device 30 (Step S311: No). When the communication is established (Step S311: Yes), the transmission requesting unit 51a determines whether the imaging interval D1 is completely received from the control unit 51 (Step S312). When the imaging interval is not completely received (Step S312: No), the transmission requesting unit 51a transmits transmission requests to the receiving device 30 via the communication unit 55 at the certain request interval d1, similarly to Step S102 of FIG. 4 (Step S313). In this case, the transmission of the transmission request in Step S313 is continued until image data is transmitted from the receiving device 30 in response to the transmission request (Step S314: No). The received imaging interval D1 is saved in, for example, a predetermined memory area. Therefore, the transmission requesting unit 51a can perform the determination of Step S312 by confirming whether the imaging time D1 is saved in the memory area.

When the reception of image data transmitted from the receiving device 30 is started in response to the transmission request of Step S313 (Step S314: Yes), the transmission requesting unit 51a waits until the reception of image data is completed (Step S315: No). After that, when the reception of image data is completed (Step S315: Yes), the transmission requesting unit 51a returns the control to Step S312 and again executes the subsequent operations.

On the other hand, when the imaging interval D1 is completely received as the determination result of Step S312 (Step S312: Yes), the transmission requesting unit 51a (Step S312: Yes) moves the control to Step s316 and sets the imaging interval D1 as the request interval d2. After that, the transmission requesting unit 51a transmits a transmission request to the receiving device 30 via the communication unit 55 at a timing obtained by adding the request interval d2 to the timing at which the previous transmission request is transmitted (Step S317). For example, as illustrated in FIG. 12, a transmission request Req22 is transmitted to the receiving device 30 at a timing t22 obtained by adding the request interval d2 to a timing t21 at which a transmission request Req21 is finally transmitted in Step S313. After that, the transmission requesting unit 51a returns the control to Step S317 and then repeats to transmit the transmission request at the request interval d2.

In the present embodiment, the transmission requests are transmitted at the first time interval (request interval d1) smaller than the predetermined time interval (imaging interval D1) at which the capsule medical device 10 transmits intra-subject images, from the communication establishment with the receiving device 30 connected as a slave to the reception of at least one image data. Therefore, the timing at which the receiving device 30 can first transmit image data can be specified by a simple procedure. Moreover, after at least two image data are received, the imaging interval D1 is calculated from the time stamps added to the two image data and the transmission requests are transmitted by using the imaging interval D1 as the request interval d2 (the second time interval). Therefore, information exchanged between the receiving device 30 and the information processing device 50 can be reduced after at least two image data are received. Furthermore, image data are acquired and displayed at the second time interval (request interval d2) equal to the imaging interval D1. Therefore, image data for intra-subject images acquired by the capsule medical device 10 can be displayed to the user in substantially real time. In this manner, according to the present embodiment, intra-subject images that are in-vivo information acquired by the capsule medical device 10 can be displayed to the user in substantially real time by simple procedures and little communications traffic.

Figure 13:
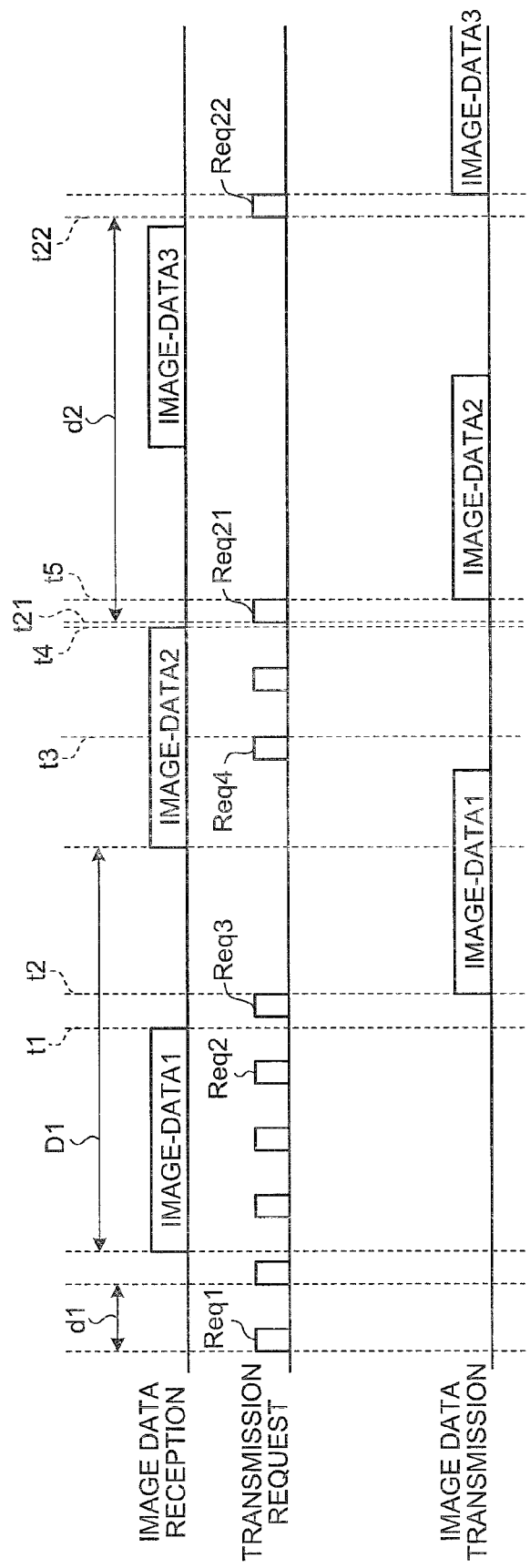
FIG. 13 is a timing chart of data that is transmitted and received between the receiving device and the information processing device according to an alternative example of the third embodiment of the present invention.

In the present embodiment, similarly to the first embodiment of the present invention, the control unit 31 of the receiving device 30 transmits the non-response (see FIG. 12) to the information processing device 50 when the control unit 31 cannot transmit image data. However, the present invention is not limited to this. For example, as illustrated in an alternative example of FIG. 13, the control unit 31 may not transmit the non-response when image data to be transmitted is not present. In this case, the control unit 31 cancels the input transmission request. By operating as above, an amount of signal transmitted and received between the receiving device 30 and the information processing device 50 can be reduced.

Moreover, in the present embodiment, the imaging interval D1 is calculated from the time stamps added to the continuously received two image data. However, the present invention is not limited to this. For example, the imaging interval D1 can be calculated from time stamps added to two or more image data that are captured continuously or discontinuously. In this case, "continuity" means that images are input into the receiving device 30 continuously and serially and "discontinuity" means that images are input into the receiving device 30 discontinuously and serially. Therefore, among discontinuous image data, it is expected that one or more image data are input into the receiving device 30.

Fourth Embodiment

Next, it will be in detail explained about the configuration and operation of a medical system according to the fourth embodiment of the present invention with reference to the drawings. In addition, for simplification of explanation about the configuration or operation similar to that of any one of the first to third embodiments of the present invention, the detailed description is omitted by putting the same symbols.

The medical system according to the fourth embodiment can have the configuration similar to that of the medical system 1 that is exemplified in the first embodiment of the present invention. However, in the fourth embodiment, procedures by which the information processing device 50 acquires image data from the receiving device 30 are different from those in the first to third embodiments.

In the fourth embodiment, the time interval (imaging interval D1) at which the capsule medical device 10 acquires intra-subject images is not previously determined. Therefore, in the present embodiment, a reception interval D3 at which the information processing device 50 receives image data is specified and the reception interval D3 is set as a request interval d3.

Next, it will be explained about procedures by which the information processing device 50 acquires image data from the receiving device 30 in consideration of an operation of the transmission requesting unit 51a of the information processing device 50 and a timing chart of data transmitted and received between the receiving device 30 and the information processing device 50.

Figure 14:
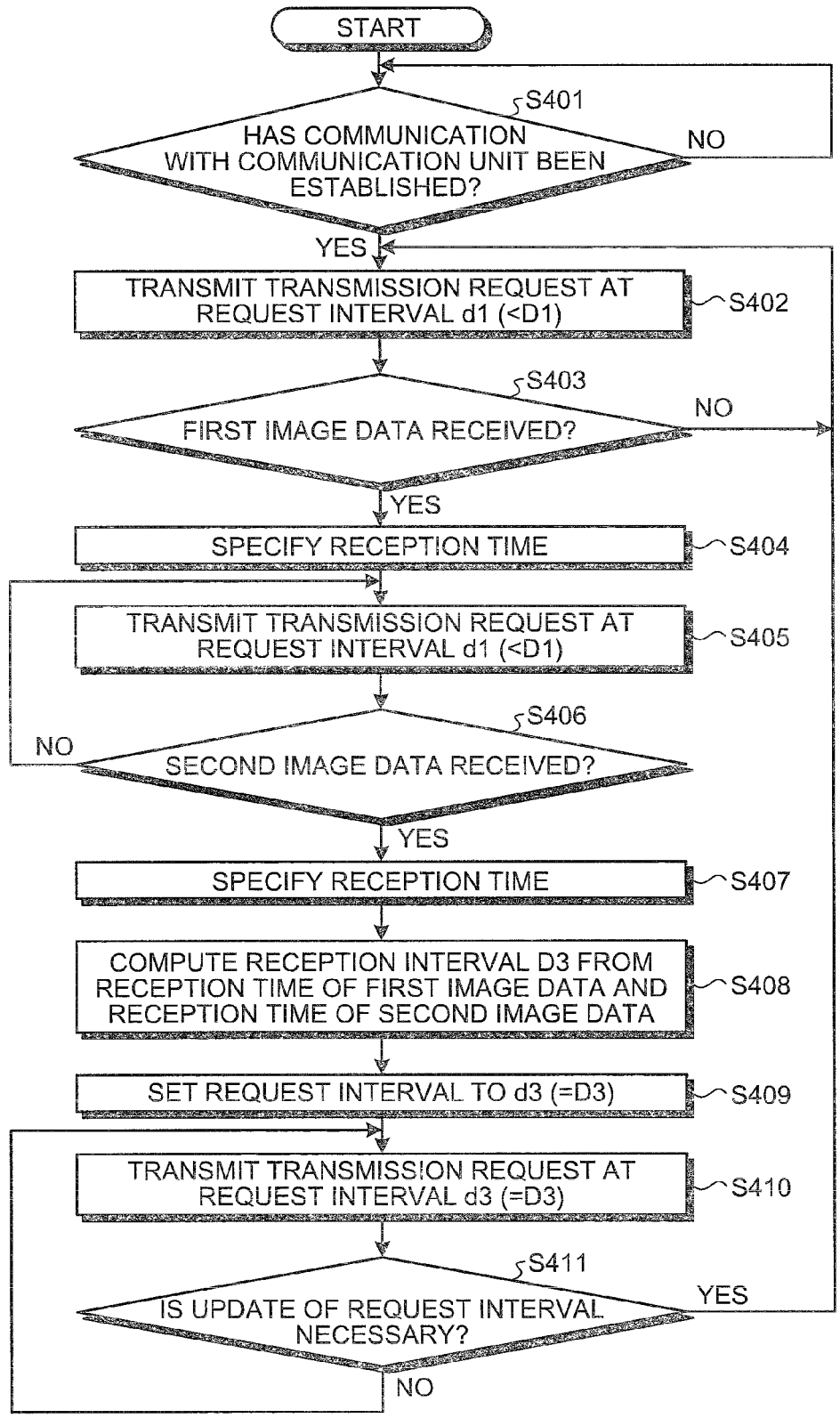
FIG. 14 is a flowchart illustrating operations performed by the transmission requesting unit in the information processing device according to the fourth embodiment of the present invention.
Figure 15:
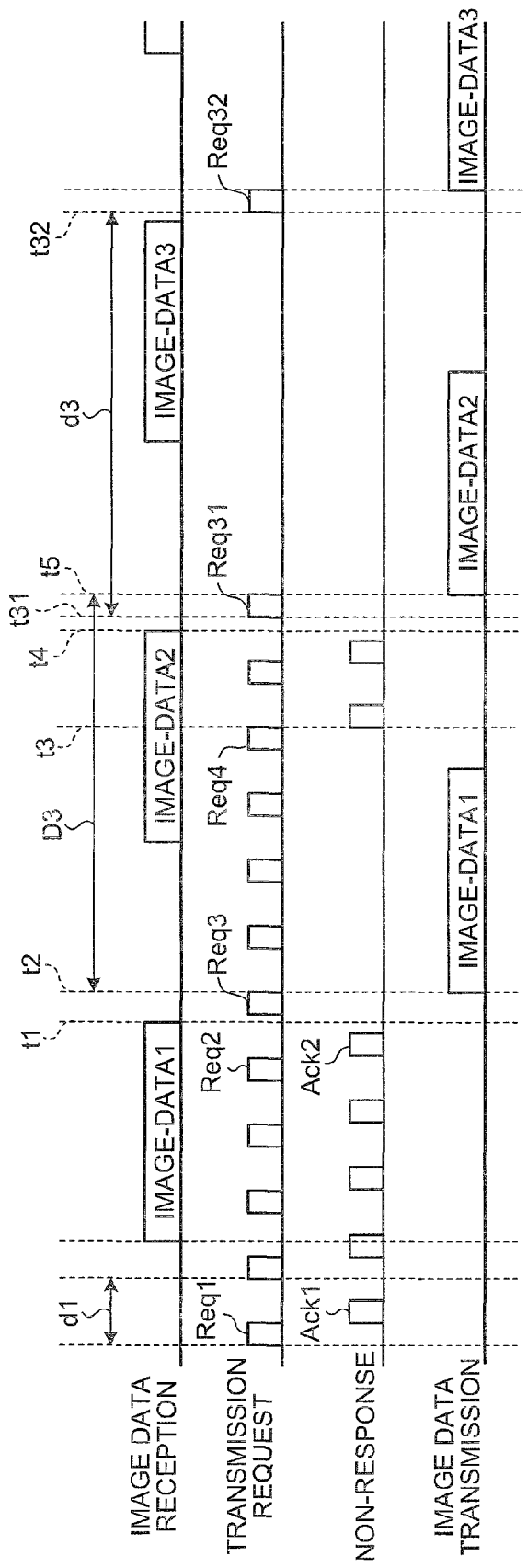
FIG. 15 is a timing chart of data that is transmitted and received between the receiving device and the information processing device according to the fourth embodiment of the present invention.

FIG. 14 is a flowchart illustrating operations of the transmission requesting unit 51a of the information processing device 50 according to the fourth embodiment. FIG. 15 is a timing chart of data that is transmitted and received between the receiving device 30 and the information processing device 50. The operation illustrated in FIG. 14 is terminated by interrupt handling performed by the control unit 51, for example, when the control unit 51 detects that communication between the receiving device 30 and the information processing device 50 is cut off.

As illustrated in FIG. 14, the transmission requesting unit 51a, which is executed in the control unit 51 of the information processing device 50, waits until the communication unit 55 establishes communication with the communication unit 35 of the receiving device 30 (Step S401: No). When the communication is established (Step S401: Yes), the transmission requesting unit 51a transmits transmission requests to the receiving device 30 via the communication unit 55 at the certain request interval d1 similarly to Step S102 of FIG. 4 (Step S402). The transmission of the transmission request in the Step S402 is continued until a first image data is transmitted from the receiving device 30 in response to the transmission request (Step S403: No).

When the first image data is received from the receiving device 30 in response to the transmission request of Step S402 (Step S403: Yes), the transmission requesting unit 51a specifies a time (reception time) at which the first image data is received (Step S404). For example, the reception time can be a timing t2 at which the reception of image-data1 is started as illustrated in FIG. 15. However, the present invention is not limited to this. For example, the reception time can be a time at which the reception of the image-data1 is completed.

Moreover, the transmission requesting unit 51a continues to transmit the transmission request of Step S402 to the receiving device 30 via the communication unit 55 at the certain request interval d1 (Step S405). The transmission of the transmission request in the Step S405 is continued until a second image data is transmitted from the receiving device 30 in response to the transmission request (Step S406: No).

When the second image data is received from the receiving device 30 in response to the transmission request of Step S405 (Step S406: Yes), the transmission requesting unit 51a specifies a time (reception time) at which the second image data is received similarly to Step S404 (Step S407). For example, the reception time can be a timing t5 at which the reception of image-data2 is started as illustrated in FIG. 15. However, the present invention is not limited to this. For example, the reception time can be a time at which the reception of the image-data2 is completed. In this way, the reception time can be transformed in various ways in accordance with the reception time of the image-data1.

When the reception times of two image data are specified in this way, the transmission requesting unit 51a computes the reception interval D3 from the two reception times (Step S408). For example, the reception interval can be calculated by subtracting the reception time (timing t2) of the first image-data1 from the reception time (timing t5) of the second image-data2.

When the reception interval D3 is computed in this way, the transmission requesting unit 51a sets the reception interval D3 as the request interval d3 (Step S409). After that, the transmission requesting unit 51a transmits a transmission request to the receiving device 30 via the communication unit 55 at a timing obtained by adding the request interval d3 to the timing at which the previous transmission request is transmitted (Step S410). For example, as illustrated in FIG. 15, the transmission requesting unit 51a transmits a transmission request Req32 to the receiving device 30 at a timing t32 obtained by adding the request interval d3 to a timing t31 at which a transmission request Req31 is finally transmitted in Step S405.

Next, the transmission requesting unit 51a determines whether the request interval d3 should be updated (Step S411). For example, the present invention can have a configuration that the request interval d3 is updated when the predetermined number of frame images is received. In this case, the predetermined number of frame images that acts as the criterion for determination can be set based on a maximum error of the request interval d3 to the imaging interval D1. The maximum error is calculated from clock cycles that act as the criterion for operations in the information processing device 50, cycles for the request interval d1, and the like. However, the present invention is not limited to this. The request interval d3 can be transformed in various ways, for example, when the non-response is sent back with respect to the transmission request transmitted at the request interval d3.

According to the determination of Step S411, when the request interval d3 should be updated (Step S411: Yes), the transmission requesting unit 51a returns the control to Step S402 and again executes the subsequent operations to reset the request interval d3. On the other hand, when the request interval d3 should not be updated (Step S411: No), the transmission requesting unit 51a returns the control to Step S410 and repeats to transmit the transmission request at the request interval d3 until the request interval d3 should be updated.

In the present embodiment, the transmission requests are transmitted at the first time interval (request interval d1) smaller than the predetermined time interval (imaging interval D1) at which the capsule medical device 10 transmits intra-subject images, from the communication establishment with the receiving device 30 connected as a slave to the reception of at least one image data. Therefore, the timing at which the receiving device 30 can first transmit image data can be specified by a simple procedure. Moreover, after at least two image data are received, the reception interval D3 for the two image data is calculated and the transmission requests are transmitted by using the reception interval D3 as the request interval d3 (the second time interval). Therefore, information exchanged between the receiving device 30 and the information processing device 50 can be reduced after at least two image data are received. Furthermore, image data are acquired and displayed at the second time interval (request interval d3) equal to the imaging interval D1. Therefore, image data for intra-subject images acquired by the capsule medical device 10 can be displayed to the user in substantially real time. In this manner, according to the present embodiment, intra-subject images that are in-vivo information acquired by the capsule medical device 10 can be displayed to the user in substantially real time by simple procedures and little communications traffic.

Figure 16:
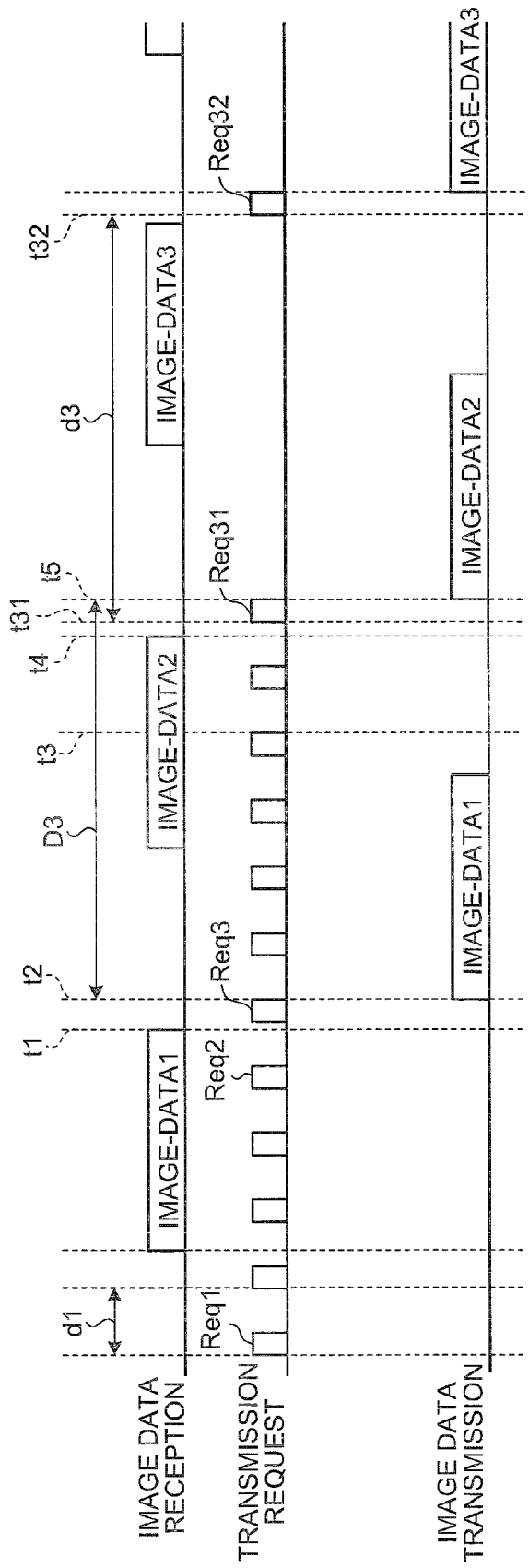
FIG. 16 is a timing chart of data that is transmitted and received between the receiving device and the information processing device according to an alternative example of the fourth embodiment of the present invention.

In the present embodiment, similarly to the first embodiment of the present invention, the control unit 31 of the receiving device 30 transmits the non-response (see FIG. 15) to the information processing device 50 when the control unit 31 cannot transmit image data. However, the present invention is not limited to this. For example, as illustrated in an alternative example of FIG. 16, the control unit 31 may not transmit the non-response when image data to be transmitted is not present. In this case, the control unit 31 cancels the input transmission request. By operating as above, an amount of signal transmitted and received between the receiving device 30 and the information processing device 50 can be reduced.

Moreover, the present embodiment has the configuration that the request interval d3 is computed from the reception interval D3 for the continuously received two image data. However, the present invention is not limited to this. For example, the request interval d3 can be computed from the reception interval of two or more continuous or discontinuous image data.

Fifth Embodiment

Next, it will be in detail explained about the configuration and operation of a medical system according to the fifth embodiment of the present invention with reference to the drawings. In addition, for simplification of explanation about the configuration or operation similar to that of any one of the first to fifth embodiments of the present invention, the detailed description is omitted by putting the same symbols.

The medical system according to the fifth embodiment can have the configuration similar to that of the medical system 1 that is exemplified in the first embodiment of the present invention. However, in the fifth embodiment, procedures by which the information processing device 50 acquires image data from the receiving device 30 are different from those in the first to fourth embodiments.

Moreover, in the fifth embodiment, the information processing device 50 waits receiving image data for a transmission request from the receiving device 30 that receives the transmission request and transmits the next transmission request after the reception of image data.

Next, it will be explained about procedures by which the information processing device 50 acquires image data from the receiving device 30 in consideration of an operation of the transmission requesting unit 51a of the information processing device 50 and a timing chart of data transmitted and received between the receiving device 30 and the information processing device 50.

Figure 17:
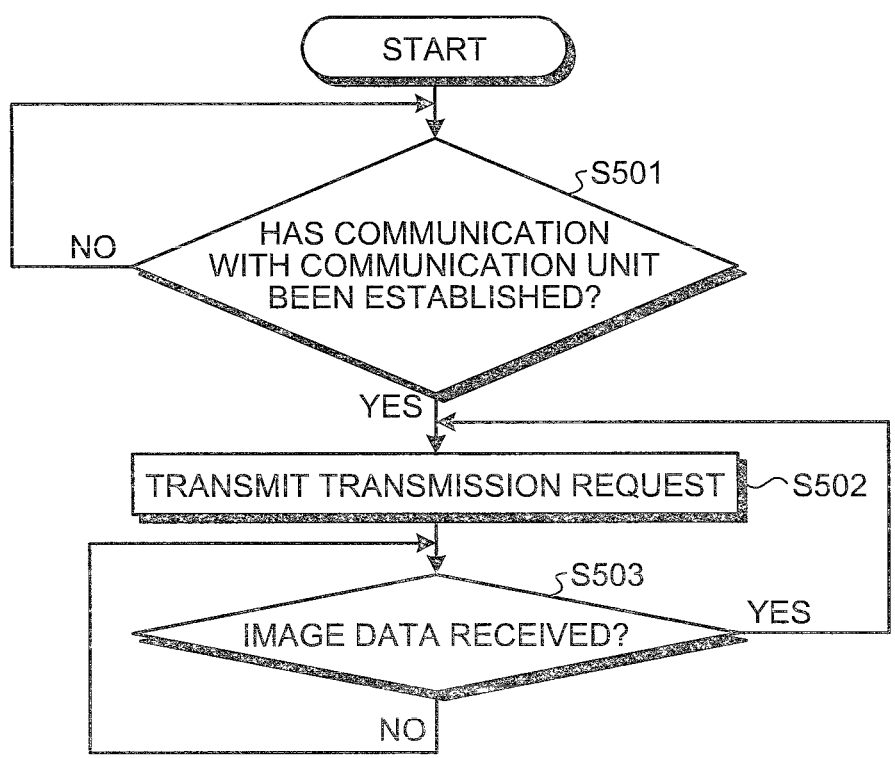
FIG. 17 is a flowchart illustrating operations performed by the transmission requesting unit in the information processing device according to the fifth embodiment of the present invention.
Figure 18:
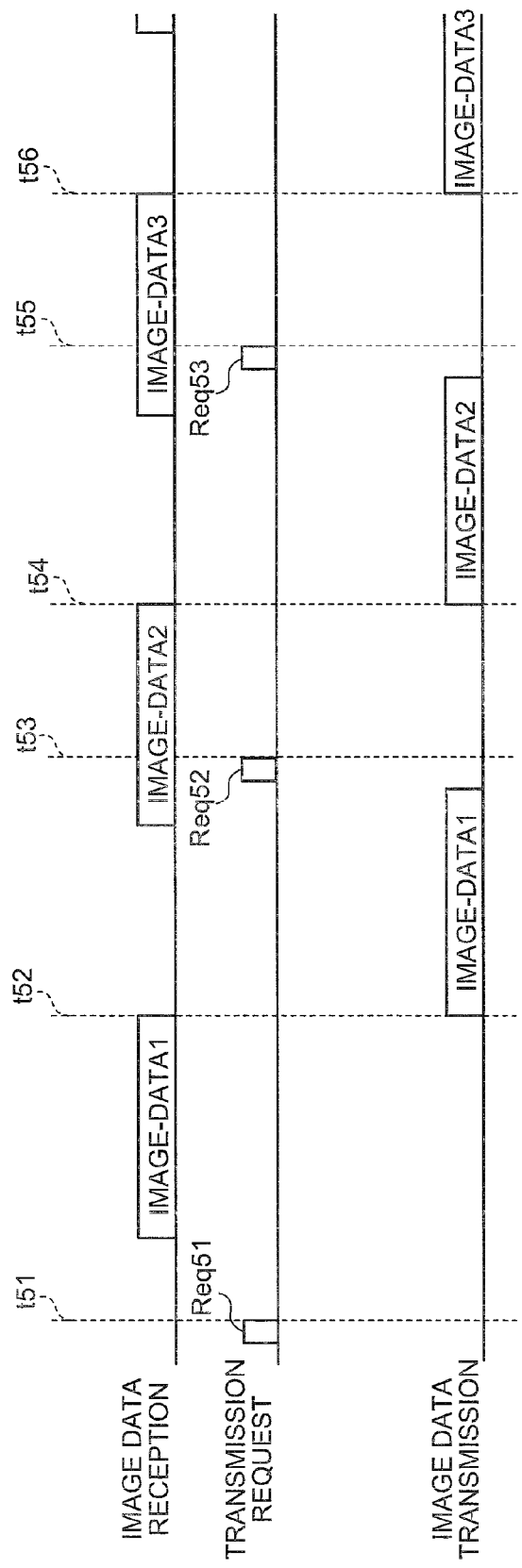
FIG. 18 is a timing chart of data that is transmitted and received between the receiving device and the information processing device according to the fifth embodiment of the present invention.

FIG. 17 is a flowchart illustrating operations of the transmission requesting unit 51a of the information processing device 50 according to the fifth embodiment. FIG. 18 is a timing chart of data that is transmitted and received between the receiving device 30 and the information processing device 50. The operation illustrated in FIG. 17 is terminated by interrupt handling performed by the control unit 51, for example, when the control unit 51 detects that communication between the receiving device 30 and the information processing device 50 is cut off.

As illustrated in FIG. 17, the transmission requesting unit 51a, which is executed in the control unit 51 of the information processing device 50, waits until the communication unit 55 establishes communication with the communication unit 35 of the receiving device 30 (Step S501: No). When the communication is established (Step S501: Yes), the transmission requesting unit 51a first transmits a transmission request to the receiving device 30 via the communication unit 55 (Step S502) and waits until the information processing device 50 receives image data from the receiving device 30 with respect to the transmission request (Step S503: No).

For example, as illustrated in FIG. 18, the receiving device 30 does not yet receive transmittable image data at a timing t51 at which a first transmission request Req51 is transmitted. In this case, the receiving device 30 maintains as a pending request the transmission request Req51 received from the information processing device 50. After that, when the receiving device 30 completes to receive image-data1 at a timing t52, the receiving device 30 transmits the image-data1 to the information processing device 50 as transmittable image data.

On the other hand, when image data is received from the receiving device 30 (Step S503: Yes), the transmission requesting unit 51a returns the control to Step S502 and then repeats to transmit a transmission request and to wait the reception of image data. For example, as illustrated in FIG. 18, when image-data1 is completely received or completely stored in the storage unit 34, the transmission requesting unit 51a transmits a transmission request Req52 for the next image data to the receiving device 30. The receiving device 30 does not yet have transmittable image data at a timing t53 at which the receiving device 30 receives the transmission request Req52. Therefore, the receiving device 30 maintains the transmission request Req52 as a pending request and transmits the next image-data2 to the information processing device 50 at a timing t54 at which the image-data2 is completely received or completely stored in the storage unit 34. Similarly, the receiving device 30 maintains the accepted transmission request Req53 as a pending request at a timing t55 and transmits the next image-data3 to the information processing device 50 at a timing t56 at which the image-data3 is completely received or completely stored in the storage unit 34.

In this way, the receiving device 30 waits until image data is received with respect to a transmission request transmitted from the information processing device 50 and maintains the transmission request as a pending request when transmittable image data is not present with respect to the transmission request. Therefore, the exchanges between the information processing device 50 and the receiving device 30 can be simplified regardless of whether the imaging interval D1 is clear in the information processing device 50. Moreover, the information processing device 50 receives the image data corresponding to the previous transmission request and then transmits the next transmission request to receive and display image data corresponding to the next. Therefore, in-vivo information can be acquired in substantially real time by simple procedures and little communications traffic. As a result, image data that is in-vivo information acquired by the capsule medical device 10 can be displayed to the user in substantially real time by simple procedures and little communications traffic.

Various types of programs for realizing operations of the information processing device in each embodiment described above can be recorded in a recording medium such as CD-ROM or DVD-ROM.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An in-vivo information display device comprising:
a communication unit that communicates with a receiving device that receives in-vivo information transmitted, at an acquisition interval of the in-vivo information, from a body-insertable device that is introduced into a subject and acquires the in-vivo information regarding an inside of the subject;
a transmission requesting unit that transmits a transmission request for the in-vivo information to the receiving device via the communication unit; and
a display unit that displays the in-vivo information received via the communication unit from the receiving device in response to the transmission request, wherein
the transmission requesting unit transmits the transmission request to the receiving device at a first time interval smaller than the acquisition interval, and the transmission requesting unit transmits the transmission request to the receiving device at a second time interval which is equal to the acquisition interval when reception of one or more the in-vivo information is started.

2. The in-vivo information display device according to claim 1, wherein the transmission requesting unit computes the second time interval based on a time interval at which the plurality of in-vivo information is received.

3. The in-vivo information display device according to claim 2, wherein the transmission requesting unit computes and updates the second time interval whenever a predetermined number of the in-vivo information is received.

4. The in-vivo information display device according to claim 1, wherein
the in-vivo information includes a time stamp indicative of time information, and
the transmission requesting unit computes the second time interval based on time stamps included in the plurality of in-vivo information.

5. The in-vivo information display device according to claim 4, wherein the time stamp indicates a time at which the body-insertable device acquires the in-vivo information, a time at which the receiving device receives the in-vivo information from the body-insertable device, or a time at which the receiving device stores the in-vivo information received from the body-insertable device in a predetermined storage area.

6. The in-vivo information display device according to claim 4, wherein the transmission requesting unit computes and updates the second time interval whenever a predetermined number of the in-vivo information is received.

7. The in-vivo information display device according to claim 1, wherein the in-vivo information includes at least one of an intra-subject image, a temperature, a pressure, and a pH value.

8. An in-vivo information display system comprising:
a body-insertable device that is introduced into a subject and includes an in-vivo information acquiring unit that acquires information regarding an inside of the subject and a transmitting unit that transmits the in-vivo information as a radio signal at an acquisition interval of the in-vivo information;
a receiving device that is arranged outside the subject and includes a receiving unit that receives the in-vivo information transmitted from the transmitting unit and a first communication unit that communicates via a predetermined line; and
an in-vivo information display device that includes a second communication unit that communicates with the first communication unit via the predetermined line and a display unit that displays the in-vivo information received via the second communication unit, wherein
the in-vivo information display device further includes a transmission requesting unit that transmits a transmission request for the in-vivo information to the receiving device via the second communication unit at a first time interval smaller than the acquisition interval, and that transmits the transmission request to the receiving device via the second communication unit at a second time interval which is equal to the acquisition interval when reception of one or more the in-vivo information is started, and
the receiving device transmits the in-vivo information received from the body-insertable device to the in-vivo information display device via the first communication unit in response to the transmission request.

9. The in-vivo information display system according to claim 8, wherein the transmission requesting unit computes the second time interval based on a time interval at which the plurality of in-vivo information is received.

10. The in-vivo information display device according to claim 9, wherein the transmission requesting unit computes and updates the second time interval whenever a predetermined number of the in-vivo information is received.

11. The in-vivo information display system according to claim 8, wherein
the in-vivo information includes a time stamp indicative of time information, and
the transmission requesting unit computes the second time interval based on time stamps included in the plurality of in-vivo information.

12. The in-vivo information display system according to claim 11, wherein the time stamp indicates a time at which the body-insertable device acquires the in-vivo information, a time at which the receiving device receives the in-vivo information from the body-insertable device, or a time at which the receiving device stores the in-vivo information received from the body-insertable device in a predetermined storage area.

13. The in-vivo information display system according to claim 11, wherein the transmission requesting unit computes and updates the second time interval whenever a predetermined number of the in-vivo information is received.

14. The in-vivo information display system according to claim 8, wherein the in-vivo information includes at least one of an intra-subject image, a temperature, a pressure, and a pH value.

15. An in-vivo information display method comprising:
transmitting a transmission request for in-vivo information to a receiving device that receives the in-vivo information transmitted, at an acquisition interval of the in-vivo information, from a body-insertable device that is introduced into an inside of a subject and acquires the in-vivo information regarding the inside of the subject;
receiving the in-vivo information transmitted from the receiving device in response to the transmission request; and displaying the received in-vivo information, wherein
the transmitting a transmission request includes
transmitting the transmission request to the receiving device at a first time interval smaller than the acquisition interval; and
transmitting the transmission request to the receiving device at a second time interval which is equal to the acquisition interval when reception of one or more the in-vivo information is started.

16. The in-vivo information display method according to claim 15, wherein the transmitting the transmission request further includes, when receiving the plurality of in-vivo information in response to a plurality of transmission requests transmitted at the first time interval, computing the second time interval based on a reception time interval of the plurality of in-vivo information.

17. The in-vivo information display method according to claim 16, wherein the computing the second time interval includes computing and updating the second time interval whenever a predetermined number of the in-vivo information is received.

18. The in-vivo information display method according to claim 15, wherein
the transmitting the transmission request further includes computing the second time interval based on time stamps respectively included in the plurality of in-vivo information when the plurality of in-vivo information is received in response to a plurality of transmission requests transmitted at the first time interval, and
the in-vivo information includes a time stamp indicative of time information.

19. The in-vivo information display method according to claim 18, wherein the computing the second time interval includes computing and updating the second time interval whenever a predetermined number of the in-vivo information is received.

20. A computer program product having a computer readable medium including programmed instructions for operating an information processing device that can communicate with a receiving device that receives in-vivo information transmitted, at an acquisition interval of the in-vivo information, from a body-insertable device, which is introduced into an inside of a subject and acquires the in-vivo information regarding the inside of the subject, wherein the instructions, when executed by a computer, cause the computer to perform:
transmitting a transmission request for the in-vivo information to the receiving device;
receiving the in-vivo information transmitted from the receiving device in response to the transmission request; and
displaying the received in-vivo information, and
the transmitting a transmission request including:
transmitting the transmission request to the receiving device at a first time interval smaller than the acquisition interval; and
transmitting the transmission request to the receiving device at a second time interval which is equal to the acquisition interval when the information processing device starts to receive one or more the in-vivo information.

* * * * *